United States Patent
Spohn et al.

(10) Patent No.: US 10,898,638 B2
(45) Date of Patent: Jan. 26, 2021

(54) SYSTEM AND METHOD FOR IMPROVED FLUID DELIVERY IN MULTI-FLUID INJECTOR SYSTEMS

(71) Applicant: BAYER HEALTHCARE LLC, Whippany, NJ (US)

(72) Inventors: Michael Spohn, Fenelton, PA (US); Ralph Schriver, Tarentum, PA (US); Arthur E. Uber, III, Pittsburgh, PA (US); Ronald Heller, Monroeville, PA (US); Kevin Cowan, Allison Park, PA (US); Barry Tucker, Verona, PA (US); Edward Rhinehart, Murrysville, PA (US); Timothy Newing, Thornleigh (AU)

(73) Assignee: BAYER HEALTHCARE LLC, Whippany, NJ (US)

( * ) Notice: Subject to any disclaimer, the term of this patent is extended or adjusted under 35 U.S.C. 154(b) by 225 days.

(21) Appl. No.: 16/081,202

(22) PCT Filed: Mar. 3, 2017

(86) PCT No.: PCT/US2017/020637
§ 371 (c)(1),
(2) Date: Aug. 30, 2018

(87) PCT Pub. No.: WO2017/152036
PCT Pub. Date: Sep. 8, 2017

(65) Prior Publication Data
US 2019/0083699 A1      Mar. 21, 2019

Related U.S. Application Data

(60) Provisional application No. 62/303,050, filed on Mar. 3, 2016.

(51) Int. Cl.
A61M 5/14       (2006.01)
A61M 5/145      (2006.01)
(Continued)

(52) U.S. Cl.
CPC .......... *A61M 5/1408* (2013.01); *A61M 5/007* (2013.01); *A61M 5/14546* (2013.01);
(Continued)

(58) Field of Classification Search
CPC .. A61M 5/007; A61M 5/14546; A61M 25/10; A61M 25/10182; A61M 25/1011;
(Continued)

(56) References Cited

U.S. PATENT DOCUMENTS 383,858 A      6/1888   Campbell et al.
3,349,713 A    10/1967  Fassbender
(Continued)

FOREIGN PATENT DOCUMENTS

AU     7381796 A    4/1997
CA     2045070 A1   2/1992
(Continued)

OTHER PUBLICATIONS

European Search Report and Opinion dated Nov. 21, 2013 from EP No. 13004902.6.
(Continued)

*Primary Examiner* — Manuel A Mendez
(74) *Attorney, Agent, or Firm* — Joseph L. Kent; David Schramm; James R. Stevenson

(57) ABSTRACT

A method of maintaining an overall flow rate during a sequential delivery of at least two fluids to a patient's blood vessel includes delivering at least a first fluid into the patient's blood vessel at a first flow rate, delivering at least a second fluid into the patient's blood vessel at a second flow rate, and adjusting at least one of a first flow profile of the
(Continued)

first flow rate and a second flow profile of the second flow rate to dampen a transient increase in the overall flow rate during a transition between delivering one of the first fluid and the second fluid to delivering the other of the first fluid and the second fluid.

20 Claims, 20 Drawing Sheets

(51) Int. Cl.
*A61M 5/00* (2006.01)
*A61M 5/142* (2006.01)
(52) U.S. Cl.
CPC .......... *A61M 5/14566* (2013.01); *A61M 2005/14208* (2013.01); *A61M 2005/14553* (2013.01); *A61M 2205/3331* (2013.01); *A61M 2205/3334* (2013.01); *A61M 2205/50* (2013.01)
(58) Field of Classification Search
CPC ....... A61M 5/19; A61M 25/104; A61B 17/22; A61F 7/12
See application file for complete search history.

(56) References Cited

U.S. PATENT DOCUMENTS

| | | |
|---|---|---|
| 3,520,295 A | 7/1970 | Paul |
| 3,523,523 A | 8/1970 | Henrich |
| 3,623,474 A | 11/1971 | Heilman |
| 3,701,345 A | 10/1972 | Heilman |
| 3,755,655 A | 8/1973 | Senecal |
| 3,793,600 A | 2/1974 | Grosbard |
| 3,812,843 A | 5/1974 | Wootten et al. |
| 3,817,843 A | 6/1974 | Barrett |
| 3,839,708 A | 10/1974 | Lyons et al. |
| 3,888,239 A | 6/1975 | Rubinstein |
| 3,895,220 A | 7/1975 | Nelson et al. |
| 3,898,983 A | 8/1975 | Elam |
| 3,927,955 A | 12/1975 | Spinosa et al. |
| 3,941,126 A | 3/1976 | Dietrich et al. |
| 3,958,103 A | 5/1976 | Oka et al. |
| 3,968,195 A | 7/1976 | Bishop |
| 3,995,381 A | 12/1976 | Manfred et al. |
| 4,001,549 A | 1/1977 | Corwin |
| 4,006,736 A | 2/1977 | Kranys et al. |
| 4,038,981 A | 8/1977 | Lefevre et al. |
| 4,044,757 A | 8/1977 | McWhorter et al. |
| 4,090,502 A | 5/1978 | Tajika |
| 4,135,247 A | 1/1979 | Gordon et al. |
| 4,151,845 A | 5/1979 | Clemens |
| 4,187,057 A | 2/1980 | Xanthopoulos |
| 4,191,183 A | 3/1980 | Mendelson |
| 4,199,000 A | 4/1980 | Edstrom |
| 4,207,871 A | 6/1980 | Jenkins |
| 4,223,675 A | 9/1980 | Williams |
| 4,262,824 A | 4/1981 | Hrynewycz |
| 4,263,916 A | 4/1981 | Brooks et al. |
| 4,280,494 A | 7/1981 | Cosgrove, Jr. et al. |
| 4,284,073 A | 8/1981 | Krause et al. |
| 4,315,247 A | 2/1982 | Germanton |
| 4,319,568 A | 3/1982 | Tregoning |
| 4,340,153 A | 7/1982 | Spivey |
| 4,341,153 A | 7/1982 | Bowser |
| 4,392,847 A | 7/1983 | Whitney et al. |
| 4,392,849 A | 7/1983 | Petre et al. |
| 4,396,385 A | 8/1983 | Kelly et al. |
| 4,402,310 A | 9/1983 | Kimura |
| 4,409,966 A | 10/1983 | Lambrecht et al. |
| 4,434,820 A | 3/1984 | Glass |
| 4,434,822 A | 3/1984 | Bellamy et al. |
| 4,444,198 A | 4/1984 | Petre |
| 4,447,230 A | 5/1984 | Gula et al. |
| 4,448,200 A | 5/1984 | Brooks et al. |
| 4,474,476 A | 10/1984 | Thomsen |
| 4,477,923 A | 10/1984 | Baumann et al. |
| 4,479,760 A | 10/1984 | Bilstad et al. |
| 4,479,761 A | 10/1984 | Bilstad et al. |
| 4,479,762 A | 10/1984 | Bilstad et al. |
| 4,504,908 A | 3/1985 | Riederer et al. |
| 4,509,526 A | 4/1985 | Barnes et al. |
| 4,512,764 A | 4/1985 | Wunsch |
| 4,542,459 A | 9/1985 | Riederer |
| 4,544,949 A | 10/1985 | Kurihara |
| 4,551,133 A | 11/1985 | Zegers De Beyl et al. |
| 4,552,130 A | 11/1985 | Kinoshita |
| 4,559,036 A | 12/1985 | Wunsch |
| 4,563,175 A | 1/1986 | LaFond |
| 4,578,802 A | 3/1986 | Itoh |
| 4,585,009 A | 4/1986 | Barker et al. |
| 4,585,941 A | 4/1986 | Bergner |
| 4,610,670 A | 9/1986 | Spencer |
| 4,610,790 A | 9/1986 | Reti et al. |
| 4,611,340 A | 9/1986 | Okazaki |
| 4,612,572 A | 9/1986 | Komatsu et al. |
| 4,625,494 A | 12/1986 | Iwatschenko et al. |
| 4,626,144 A | 12/1986 | Berner |
| 4,633,307 A | 12/1986 | Honda |
| 4,634,426 A | 1/1987 | Kamen |
| 4,636,144 A | 1/1987 | Abe et al. |
| 4,655,197 A | 4/1987 | Atkinson |
| 4,662,906 A | 5/1987 | Matkovich et al. |
| 4,672,651 A | 6/1987 | Horiba et al. |
| 4,676,776 A | 6/1987 | Howson |
| 4,682,170 A | 7/1987 | Kubota et al. |
| 4,689,670 A | 8/1987 | Okazaki |
| 4,710,166 A | 12/1987 | Thompson et al. |
| 4,723,261 A | 2/1988 | Janssen et al. |
| 4,750,643 A | 6/1988 | Wortrich |
| 4,754,786 A | 7/1988 | Roberts |
| 4,781,687 A | 11/1988 | Wall |
| 4,783,273 A | 11/1988 | Knutsson et al. |
| 4,789,014 A | 12/1988 | DiGianfilippo et al. |
| 4,793,357 A | 12/1988 | Lindstrom |
| 4,795,429 A | 1/1989 | Feldstein |
| 4,798,590 A | 1/1989 | O'Leary et al. |
| 4,804,454 A | 2/1989 | Asakura et al. |
| 4,823,833 A | 4/1989 | Hogan et al. |
| 4,835,521 A | 5/1989 | Andrejasich et al. |
| 4,836,187 A | 6/1989 | Iwakoshi et al. |
| 4,838,856 A | 6/1989 | Mulreany et al. |
| 4,840,620 A | 6/1989 | Kobayashi et al. |
| 4,844,052 A | 7/1989 | Iwakoshi et al. |
| 4,853,521 A | 8/1989 | Claeys et al. |
| 4,854,301 A | 8/1989 | Nakajima |
| 4,854,324 A | 8/1989 | Hirschman et al. |
| 4,857,056 A | 8/1989 | Talonn |
| 4,874,359 A | 10/1989 | White et al. |
| 4,879,880 A | 11/1989 | Harrison |
| 4,880,014 A | 11/1989 | Zarowitz et al. |
| 4,887,208 A | 12/1989 | Schneider et al. |
| 4,887,554 A | 12/1989 | Whitford |
| 4,901,731 A | 2/1990 | Millar |
| 4,903,705 A | 2/1990 | Imamura et al. |
| 4,913,154 A | 4/1990 | Ermert et al. |
| 4,922,916 A | 5/1990 | Ermert et al. |
| 4,925,444 A | 5/1990 | Orkin et al. |
| 4,929,818 A | 5/1990 | Bradbury et al. |
| 4,935,005 A | 6/1990 | Haines |
| 4,936,832 A | 6/1990 | Vaillancourt |
| 4,943,279 A | 7/1990 | Samiotes et al. |
| 4,943,779 A | 7/1990 | Pedersen et al. |
| 4,943,987 A | 7/1990 | Asahina et al. |
| 4,946,256 A | 8/1990 | Woodruff |
| 4,946,439 A | 8/1990 | Eggers |
| 4,947,412 A | 8/1990 | Mattson |
| 4,950,245 A | 8/1990 | Brown et al. |
| 4,954,129 A | 9/1990 | Giuliani et al. |
| 4,965,726 A | 10/1990 | Heuscher et al. |
| 4,966,579 A | 10/1990 | Polaschegg |
| 4,976,687 A | 12/1990 | Martin |
| 4,978,335 A | 12/1990 | Arthur, III |

(56) References Cited

U.S. PATENT DOCUMENTS

| | | |
|---|---|---|
| 4,981,467 A | 1/1991 | Bobo, Jr. et al. |
| 4,995,064 A | 2/1991 | Wilson et al. |
| 5,002,055 A | 3/1991 | Merki et al. |
| 5,004,472 A | 4/1991 | Wallace et al. |
| 5,009,654 A | 4/1991 | Minshall et al. |
| 5,010,473 A | 4/1991 | Jacobs |
| 5,013,173 A | 5/1991 | Shiraishi |
| 5,018,173 A | 5/1991 | Komai et al. |
| 5,032,112 A | 7/1991 | Fairchild et al. |
| 5,034,987 A | 7/1991 | Fujimoto et al. |
| 5,040,537 A | 8/1991 | Katakura |
| 5,053,002 A | 10/1991 | Barlow |
| 5,054,044 A | 10/1991 | Audon et al. |
| 5,056,568 A | 10/1991 | DiGianfilippo et al. |
| 5,059,173 A | 10/1991 | Sacco |
| 5,061,243 A | 10/1991 | Winchell et al. |
| 5,069,662 A | 12/1991 | Bodden |
| 5,078,683 A | 1/1992 | Sancoff et al. |
| 5,088,981 A | 2/1992 | Howson et al. |
| 5,100,380 A | 3/1992 | Epstein et al. |
| 5,104,374 A | 4/1992 | Bishko et al. |
| 5,104,387 A | 4/1992 | Pokorney et al. |
| 5,108,365 A | 4/1992 | Woods, Jr. |
| 5,111,492 A | 5/1992 | Klausz |
| 5,113,905 A | 5/1992 | Pruitt et al. |
| 5,123,056 A | 6/1992 | Wilson |
| 5,123,121 A | 6/1992 | Broersma |
| 5,125,018 A | 6/1992 | Asahina |
| 5,128,121 A | 7/1992 | Berg et al. |
| 5,133,336 A | 7/1992 | Savitt et al. |
| 5,135,000 A | 8/1992 | Akselrod et al. |
| 5,150,292 A | 9/1992 | Hoffmann et al. |
| 5,166,961 A | 11/1992 | Brunnett et al. |
| 5,180,895 A | 1/1993 | Briggs et al. |
| 5,180,896 A | 1/1993 | Gibby et al. |
| 5,190,744 A | 3/1993 | Rocklage et al. |
| 5,191,878 A | 3/1993 | Iida et al. |
| 5,196,007 A | 3/1993 | Ellman et al. |
| 5,199,604 A | 4/1993 | Palmer et al. |
| 5,207,642 A | 5/1993 | Orkin et al. |
| 5,215,095 A | 6/1993 | Macvicar et al. |
| 5,228,070 A | 7/1993 | Mattson |
| 5,230,614 A | 7/1993 | Zanger et al. |
| 5,242,390 A | 9/1993 | Goldrath |
| 5,249,122 A | 9/1993 | Stritzke |
| 5,249,579 A | 10/1993 | Hobbs et al. |
| 5,262,946 A | 11/1993 | Heuscher |
| 5,267,174 A | 11/1993 | Kaufman et al. |
| 5,269,756 A | 12/1993 | Dryden |
| 5,273,537 A | 12/1993 | Haskvitz et al. |
| 5,274,218 A | 12/1993 | Urata et al. |
| 5,276,614 A | 1/1994 | Heuscher |
| 5,286,252 A | 2/1994 | Tuttle et al. |
| 5,287,273 A | 2/1994 | Kupfer et al. |
| 5,300,031 A | 4/1994 | Neer et al. |
| 5,301,656 A | 4/1994 | Negoro et al. |
| 5,301,672 A | 4/1994 | Kalender |
| 5,304,126 A | 4/1994 | Epstein et al. |
| 5,310,997 A | 5/1994 | Roach et al. |
| 5,311,568 A | 5/1994 | McKee, Jr. et al. |
| 5,313,992 A | 5/1994 | Grabenkort |
| 5,317,506 A | 5/1994 | Coutre et al. |
| 5,328,463 A | 7/1994 | Barton et al. |
| 5,329,459 A | 7/1994 | Kaufman et al. |
| 5,334,141 A | 8/1994 | Carr et al. |
| 5,339,799 A | 8/1994 | Kami et al. |
| 5,349,625 A | 9/1994 | Born et al. |
| 5,349,635 A | 9/1994 | Scott |
| 5,352,979 A | 10/1994 | Conturo |
| 5,354,273 A | 10/1994 | Hagen |
| 5,361,761 A | 11/1994 | Van Lysel et al. |
| 5,362,948 A | 11/1994 | Morimoto |
| 5,368,562 A | 11/1994 | Blomquist et al. |
| 5,368,567 A | 11/1994 | Lee |
| 5,368,570 A | 11/1994 | Thompson et al. |
| 5,373,231 A | 12/1994 | Boll et al. |
| 5,376,070 A | 12/1994 | Purvis et al. |
| 5,378,231 A | 1/1995 | Johnson et al. |
| 5,382,232 A | 1/1995 | Hague et al. |
| 5,383,231 A | 1/1995 | Yamagishi |
| 5,383,858 A | 1/1995 | Reilly et al. |
| 5,385,540 A | 1/1995 | Abbott et al. |
| 5,388,139 A | 2/1995 | Beland |
| 5,392,849 A | 2/1995 | Matsunaga et al. |
| 5,400,792 A | 3/1995 | Hoebel et al. |
| 5,417,213 A | 5/1995 | Prince |
| 5,431,627 A | 7/1995 | Pastrone et al. |
| 5,433,704 A | 7/1995 | Ross et al. |
| 5,445,621 A | 8/1995 | Poli et al. |
| 5,450,847 A | 9/1995 | Kampfe et al. |
| 5,453,639 A | 9/1995 | Cronin et al. |
| 5,456,255 A | 10/1995 | Abe et al. |
| 5,458,128 A | 10/1995 | Polanyi et al. |
| 5,459,769 A | 10/1995 | Brown |
| 5,460,609 A | 10/1995 | O'Donnell |
| 5,464,391 A | 11/1995 | Devale |
| 5,468,240 A | 11/1995 | Gentelia et al. |
| 5,469,769 A | 11/1995 | Sawada et al. |
| 5,469,849 A | 11/1995 | Sasaki et al. |
| 5,472,403 A | 12/1995 | Cornacchia et al. |
| 5,474,683 A | 12/1995 | Bryant et al. |
| 5,485,831 A | 1/1996 | Holdsworth et al. |
| 5,489,265 A | 2/1996 | Montalvo et al. |
| 5,494,036 A | 2/1996 | Uber, III et al. |
| 5,494,822 A | 2/1996 | Sadri |
| 5,496,273 A | 3/1996 | Pastrone et al. |
| 5,507,412 A | 4/1996 | Ebert et al. |
| 5,515,851 A | 5/1996 | Goldstein |
| 5,522,798 A | 6/1996 | Johnson et al. |
| 5,531,679 A | 7/1996 | Schulman et al. |
| 5,531,697 A | 7/1996 | Olsen et al. |
| 5,533,978 A | 7/1996 | Teirstein |
| 5,544,215 A | 8/1996 | Shroy, Jr. et al. |
| 5,547,470 A | 8/1996 | Johnson et al. |
| 5,552,130 A | 9/1996 | Kraus et al. |
| 5,553,619 A | 9/1996 | Prince |
| 5,560,317 A | 10/1996 | Bunyan et al. |
| 5,566,092 A | 10/1996 | Wang et al. |
| 5,569,181 A | 10/1996 | Heilman et al. |
| 5,569,208 A | 10/1996 | Woelpper et al. |
| 5,573,515 A | 11/1996 | Wilson et al. |
| 5,579,767 A | 12/1996 | Prince |
| 5,583,902 A | 12/1996 | Bae et al. |
| 5,590,654 A | 1/1997 | Prince |
| 5,592,940 A | 1/1997 | Kampfe et al. |
| 5,601,086 A | 2/1997 | Pretlow, III et al. |
| 5,611,344 A | 3/1997 | Bernstein et al. |
| 5,616,124 A | 4/1997 | Hague et al. |
| 5,681,285 A | 10/1997 | Ford et al. |
| 5,687,208 A | 11/1997 | Bae et al. |
| 5,687,708 A | 11/1997 | Farnsworth et al. |
| 5,713,358 A | 2/1998 | Mistretta et al. |
| 5,724,976 A | 3/1998 | Mine et al. |
| 5,739,508 A | 4/1998 | Uber, III |
| 5,743,266 A | 4/1998 | Levene et al. |
| 5,768,405 A | 6/1998 | Makram-Ebeid |
| 5,796,862 A | 8/1998 | Pawlicki et al. |
| 5,799,649 A | 9/1998 | Prince |
| 5,800,397 A | 9/1998 | Wilson et al. |
| 5,806,519 A | 9/1998 | Evans, III et al. |
| 5,808,203 A | 9/1998 | Nolan, Jr. et al. |
| 5,827,219 A | 10/1998 | Uber, III et al. |
| 5,827,504 A | 10/1998 | Yan et al. |
| 5,840,026 A | 11/1998 | Uber, III et al. |
| 5,843,037 A | 12/1998 | Uber, III |
| 5,846,517 A | 12/1998 | Unger |
| 5,865,744 A | 2/1999 | Lemelson |
| 5,873,861 A | 2/1999 | Hitchins et al. |
| 5,881,124 A | 3/1999 | Giger et al. |
| 5,882,343 A | 3/1999 | Wilson et al. |
| 5,902,054 A | 5/1999 | Coudray |
| 5,903,454 A | 5/1999 | Hoffberg et al. |
| 5,916,165 A | 6/1999 | Duchon et al. |
| 5,920,054 A | 7/1999 | Uber, III |

(56) References Cited

U.S. PATENT DOCUMENTS

| | | |
|---|---|---|
| 5,947,935 A | 9/1999 | Rhinehart et al. |
| 5,987,347 A | 11/1999 | Khoury et al. |
| 5,988,587 A | 11/1999 | Duchon et al. |
| 6,046,225 A | 4/2000 | Maddock |
| 6,055,985 A | 5/2000 | Bae et al. |
| 6,056,902 A | 5/2000 | Hettinga |
| 6,063,052 A | 5/2000 | Uber, III et al. |
| 6,073,042 A | 6/2000 | Simonetti |
| 6,099,502 A | 8/2000 | Duchon et al. |
| 6,149,627 A | 11/2000 | Uber, III |
| 6,186,146 B1 | 2/2001 | Glickman |
| 6,201,889 B1 | 3/2001 | Vannah |
| 6,221,045 B1 | 4/2001 | Duchon et al. |
| 6,236,706 B1 | 5/2001 | Hsieh |
| 6,248,093 B1 | 6/2001 | Moberg |
| 6,306,117 B1 | 10/2001 | Uber, III |
| 6,313,131 B1 | 11/2001 | Lawyer |
| 6,317,623 B1 | 11/2001 | Griffiths et al. |
| 6,344,030 B1 | 2/2002 | Duchon et al. |
| 6,381,486 B1 | 4/2002 | Mistretta et al. |
| 6,387,098 B1 | 5/2002 | Cole et al. |
| 6,397,093 B1 | 5/2002 | Aldrich |
| 6,397,097 B1 | 5/2002 | Requardt |
| 6,402,697 B1 | 6/2002 | Calkins et al. |
| 6,423,719 B1 | 7/2002 | Lawyer |
| 6,470,889 B1 | 10/2002 | Bae et al. |
| 6,471,674 B1 | 10/2002 | Emig et al. |
| 6,478,735 B1 | 11/2002 | Pope et al. |
| 6,503,226 B1 | 1/2003 | Martinell Gisper-Sauch et al. |
| 6,520,930 B2 | 2/2003 | Critchlow et al. |
| 6,527,718 B1 | 3/2003 | Connor et al. |
| 6,554,819 B2 | 4/2003 | Reich |
| 6,556,695 B1 | 4/2003 | Packer et al. |
| 6,572,851 B2 | 6/2003 | Muramatsu et al. |
| 6,574,496 B1 | 6/2003 | Golman et al. |
| 6,575,930 B1 | 6/2003 | Trombley, III et al. |
| 6,597,938 B2 | 7/2003 | Liu |
| 6,626,862 B1 | 9/2003 | Duchon et al. |
| 6,635,030 B1 | 10/2003 | Bae et al. |
| 6,643,537 B1 | 11/2003 | Zatezalo et al. |
| 6,652,489 B2 | 11/2003 | Trocki et al. |
| 6,656,157 B1 | 12/2003 | Duchon et al. |
| 6,673,033 B1 | 1/2004 | Sciulli et al. |
| 6,685,733 B1 | 2/2004 | Dae et al. |
| 6,691,047 B1 | 2/2004 | Fredericks |
| 6,699,219 B2 | 3/2004 | Emig et al. |
| 6,754,521 B2 | 6/2004 | Prince |
| 6,775,764 B1 | 8/2004 | Batcher |
| 6,776,764 B2 | 8/2004 | Pinsky |
| 6,866,653 B2 | 3/2005 | Bae |
| 6,876,720 B2 | 4/2005 | Tsuyuki |
| 6,879,853 B2 | 4/2005 | Meaney et al. |
| 6,983,590 B2 | 1/2006 | Roelle et al. |
| 7,094,216 B2 | 8/2006 | Trombley et al. |
| 7,267,666 B1 | 9/2007 | Duchon et al. |
| 7,267,667 B2 | 9/2007 | Houde et al. |
| 7,292,720 B2 | 11/2007 | Horger et al. |
| 7,553,294 B2 | 6/2009 | Lazzaro et al. |
| 7,553,295 B2 | 6/2009 | Susi |
| 7,563,249 B2 | 7/2009 | Schriver et al. |
| 7,666,169 B2 | 2/2010 | Cowan et al. |
| 7,688,057 B2 | 3/2010 | Foss et al. |
| 7,925,330 B2 | 4/2011 | Kalafut et al. |
| 8,007,487 B2 | 8/2011 | Patrick et al. |
| 8,295,914 B2 | 10/2012 | Kalafut et al. |
| 8,377,003 B2 | 2/2013 | Wagner |
| 8,403,909 B2 | 3/2013 | Spohn et al. |
| 8,439,863 B2 | 5/2013 | Fago et al. |
| 8,486,017 B2 | 7/2013 | Masuda et al. |
| 9,101,708 B2 | 8/2015 | Small et al. |
| 9,173,995 B1 | 11/2015 | Tucker et al. |
| 9,199,033 B1 | 12/2015 | Cowan et al. |
| 9,238,099 B2 | 1/2016 | Kalafut et al. |
| 9,901,671 B2 | 2/2018 | Toews et al. |
| 9,987,413 B2 | 6/2018 | Seibold et al. |
| 10,041,483 B2 | 8/2018 | Chappel et al. |
| 10,112,008 B2 | 10/2018 | Neftel et al. |
| 2001/0027265 A1 | 10/2001 | Prince |
| 2001/0056233 A1 | 12/2001 | Uber et al. |
| 2002/0010551 A1 | 1/2002 | Wang et al. |
| 2002/0026148 A1 | 2/2002 | Uber et al. |
| 2002/0099254 A1 | 7/2002 | Movahed |
| 2002/0123702 A1 | 9/2002 | Cho |
| 2002/0151854 A1 | 10/2002 | Duchon et al. |
| 2003/0050556 A1 | 3/2003 | Uber et al. |
| 2003/0120171 A1 | 6/2003 | Diamantopoulos et al. |
| 2003/0195462 A1 | 10/2003 | Mann et al. |
| 2003/0212364 A1 | 11/2003 | Mann et al. |
| 2003/0216683 A1 | 11/2003 | Shekalim |
| 2004/0011740 A1 | 1/2004 | Bernard et al. |
| 2004/0025452 A1 | 2/2004 | McLean |
| 2004/0044302 A1 | 3/2004 | Bernard et al. |
| 2004/0064041 A1 | 4/2004 | Lazzaro et al. |
| 2004/0097806 A1 | 5/2004 | Hunter et al. |
| 2004/0162484 A1 | 8/2004 | Nemoto |
| 2004/0163655 A1 | 8/2004 | Gelfand et al. |
| 2004/0167415 A1 | 8/2004 | Gelfand et al. |
| 2004/0215144 A1 | 10/2004 | Duchon et al. |
| 2004/0254533 A1 | 12/2004 | Schriver et al. |
| 2005/0107697 A1 | 5/2005 | Berke et al. |
| 2005/0171487 A1 | 8/2005 | Haury et al. |
| 2005/0234407 A1 | 10/2005 | Spohn et al. |
| 2005/0234428 A1 | 10/2005 | Spohn et al. |
| 2006/0079765 A1 | 4/2006 | Neer et al. |
| 2006/0079843 A1 | 4/2006 | Brooks et al. |
| 2007/0129705 A1 | 6/2007 | Trombley |
| 2007/0161970 A1 | 7/2007 | Spohn et al. |
| 2007/0219496 A1 | 9/2007 | Kamen et al. |
| 2007/0276327 A1 | 11/2007 | Kalafut et al. |
| 2008/0086087 A1 | 4/2008 | Spohn et al. |
| 2008/0167621 A1 | 7/2008 | Wagner et al. |
| 2008/0183131 A1 | 7/2008 | Duchon et al. |
| 2009/0112164 A1 | 4/2009 | Reilly et al. |
| 2009/0312744 A1 | 12/2009 | Keeley et al. |
| 2010/0222768 A1 | 9/2010 | Spohn et al. |
| 2010/0262078 A1 | 10/2010 | Blomquist |
| 2010/0331779 A1 | 12/2010 | Nystrom et al. |
| 2012/0203177 A1 | 8/2012 | Lanier, Jr. et al. |
| 2012/0204997 A1 | 8/2012 | Winn et al. |
| 2013/0245604 A1 | 9/2013 | Kouyoumjian et al. |
| 2014/0027009 A1 | 1/2014 | Riley et al. |
| 2016/0331951 A1 | 11/2016 | Sokolov et al. |
| 2017/0112995 A1 | 4/2017 | Sams et al. |
| 2017/0258982 A1 | 9/2017 | Kemper |
| 2017/0343446 A1 | 11/2017 | Ciolkosz et al. |
| 2018/0133392 A1 | 5/2018 | Dembo et al. |

FOREIGN PATENT DOCUMENTS

| | | |
|---|---|---|
| CA | 2077712 A1 | 12/1993 |
| CA | 2234050 A1 | 4/1997 |
| DE | 3203594 A1 | 8/1983 |
| DE | 3726452 A1 | 2/1989 |
| DE | 4426387 A1 | 8/1995 |
| DE | 19702896 A1 | 7/1997 |
| DE | 19647701 A1 | 5/1998 |
| EP | 0121216 A1 | 10/1984 |
| EP | 0129910 A1 | 1/1985 |
| EP | 0189491 A1 | 8/1986 |
| EP | 0192786 A2 | 9/1986 |
| EP | 0245160 A1 | 11/1987 |
| EP | 0319275 A1 | 6/1989 |
| EP | 0337924 A2 | 10/1989 |
| EP | 0343501 A2 | 11/1989 |
| EP | 0364966 A1 | 4/1990 |
| EP | 0365301 A1 | 4/1990 |
| EP | 0372152 A1 | 6/1990 |
| EP | 0378896 A2 | 7/1990 |
| EP | 0429191 A2 | 5/1991 |
| EP | 0471455 A2 | 2/1992 |
| EP | 0475563 a1 | 3/1992 |
| EP | 0595474 a2 | 5/1994 |
| EP | 0600448 A2 | 6/1994 |
| EP | 0619122 A1 | 10/1994 |

(56) References Cited

FOREIGN PATENT DOCUMENTS

| | | |
|---|---|---|
| EP | 0439711 B1 | 5/1995 |
| EP | 0869738 A1 | 10/1998 |
| EP | 2990073 A1 | 3/2016 |
| FR | 2493708 A1 | 5/1982 |
| FR | 2561949 A1 | 10/1985 |
| GB | 201800 A | 8/1923 |
| GB | 2252656 A | 8/1992 |
| GB | 2328745 A | 3/1999 |
| JP | S5017781 A | 2/1975 |
| JP | S5815842 A | 1/1983 |
| JP | S59214432 A | 12/1984 |
| JP | S60194934 A | 10/1985 |
| JP | S60194935 A | 10/1985 |
| JP | S60253197 A | 12/1985 |
| JP | S62216199 A | 9/1987 |
| JP | S6340538 A | 2/1988 |
| JP | S63290547 A | 11/1988 |
| JP | H101207038 A | 8/1989 |
| JP | H02224647 A | 9/1990 |
| JP | H02234747 A | 9/1990 |
| JP | H0355040 A | 3/1991 |
| JP | H04115677 A | 4/1992 |
| JP | H0584296 A | 4/1993 |
| JP | H07178169 A | 7/1995 |
| JP | H10211198 A | 8/1998 |
| JP | 2000175900 A | 6/2000 |
| JP | 2003102724 A | 4/2003 |
| JP | 2003116843 A | 4/2003 |
| JP | 2003210456 A | 7/2003 |
| JP | 2003225234 A | 8/2003 |
| JP | 2004174008 A | 6/2004 |
| JP | 2004236849 A | 8/2004 |
| JP | 2004298550 A | 10/2004 |
| WO | 8001754 A1 | 9/1980 |
| WO | 8500292 A1 | 1/1985 |
| WO | 8803815 A1 | 6/1988 |
| WO | 9114232 A1 | 9/1991 |
| WO | 9114233 A1 | 9/1991 |
| WO | 9315658 A1 | 8/1993 |
| WO | 9325141 A1 | 12/1993 |
| WO | 9415664 A1 | 7/1994 |
| WO | 9632975 A1 | 10/1996 |
| WO | 9712550 A1 | 4/1997 |
| WO | 9820919 A1 | 5/1998 |
| WO | 9924095 A2 | 5/1999 |
| WO | 0061216 A1 | 10/2000 |
| WO | 03015633 A1 | 2/2003 |
| WO | 2004012787 A2 | 2/2004 |
| WO | 2005016165 A1 | 2/2005 |
| WO | 2006042093 A1 | 4/2006 |
| WO | 2007092618 A2 | 8/2007 |
| WO | 2007133942 A2 | 11/2007 |
| WO | 2012155035 A1 | 11/2012 |
| WO | 2013043868 A1 | 3/2013 |
| WO | 2014144651 A2 | 9/2014 |
| WO | 2015106107 A1 | 7/2015 |
| WO | 2016112163 A1 | 7/2016 |
| WO | 2017096072 A1 | 6/2017 |

OTHER PUBLICATIONS

Angelini, P., "Use of mechanical injectors during percutaneous transluminal coronary angioplasty (PTCA)," Catheterization and Cardiovascular Diagnosis, vol. 16, Issue 3, pp. 193-194, Mar. 1989.
Angiography, Catheterization and Cardiovascular Diagnosis, vol. 19, pp. 123-128, 1990.
Awai, K., et al., "Aortic and hepatic enhancement and tumor-to-liver contrast: analysis of the effect of different concentrations of contrast material at multi-detector row helical CT.," Radiology, vol. 224, Issue 3, pp. 757-763, 2002.
Awai, K., et al., "Effect of contrast material injection duration and rate on aortic peak time and peak enhancement at dynamic CT involving injection protocol with dose tailored to patient weight," Radiology, vol. 230, Issue 1, pp. 142-150, 2004.
Bae, et al."Aortic and Hepatic Contrast Medium Enhancement at CT—Part I, Prediction with a Computer Model", Radiology 1998;207:647-655.
Bae, K.T., et al., "Multiphasic Injection Method for Uniform Prolonged Vascular Enhancement at CT Angiography: Pharmacokinetic Analysis and Experimental Porcine Model," Radiology, vol. 216, Issue 3, pp. 872-880 (Sep. 2000).
Bae, K.T. et al, "Peak Contrast Enhancement in CT and MR Angiography: When Does it Occur and Why? Pharmacokinetic Study in a Porcine Model", Radiology, vol. 227, Jun. 2003, pp. 809-816.
Bae, K.T., et al., "Uniform vascular contrast enhancement and reduced contrast medium vol. achieved by using exponentially decelerated contrast material injection method," Radiology, vol. 231, Issue 3, pp. 732-736, 2004.
Baker, Aaron; et al. "Fluid Mechanics Analysis of a Spring-Loaded Jet Injector." IEEE Transactions on Biomedical Engineering, vol. 46, No. 2, Feb. 1999.
Becker, C.R., et al., "Optimal contrast application for cardiac 4-detector-row computed tomography," Investigative Radiology, vol. 38, Issue 11, pp. 690-694 (Nov. 2003).
Blomley, M.J.K. and Dawson, P., "Bolus Dynamics: Theoretical and Experimental Aspects," The Brit. J. ofRadiology, vol. 70, No. 832, pp. 351-359 (Apr. 1997).
Brunette J. et al., "Comparative rheology of low- and iso-osmolarity contrast agents at different temperature", Catheterization and Cardiovascular Interventions, 2008, vol. 71 Issue No. 1, 78-83.
Cademartiri, F. and Luccichenti, G., et al. "Sixteen-row multislice computed tomography: basic concepts, protocols, and enhanced clinical applications," Seminars in Ultrasound, CT and MRI, vol. 25, Issue 1, pp. 2-16, 2004.
Dardik, H. et al., "Remote Hydraulic Syringe Actuator," Arch. Surg., vol. 115, Issue 1, Jan. 1980.
Dawson, P. and Blomley, M., "The value of mathematical modelling in understanding contrast enhancement in CT with particular reference to the detection of hypovascular liver metastases," European Journal of Radiology, vol. 41, Issue 3, pp. 222-236 (Mar. 2002).
"Digital Injector for Angiography", Sias. (Sep. 7, 1993).
Disposable Low-Cost Catheter Tip Sensor Measures Blood Pressure during Surgery, Sensor (Jul. 1989).
European Search Report and Supplemental European Search Report from EP05849688 dated Mar. 21, 2014.
European Search Report dated Feb. 21, 2012 in European Patent Application No. 11001045.1.
European Search Report dated Jan. 30, 2003 in European Patent Application No. 02020247.9.
European Search Report dated Jun. 17, 1996 in European Patent Application No. 95202547.6.
EZ Chem Brochure, E-Z-EM, Inc. (Jul. 2007).
Fisher, M.E and Teo, K.L., "Optimal insulin infusion resulting from a mathematical model of blood glucose dynamics", IEEE Transactions on Biomedical Engineering, vol. 36, Issue 4, pp. 479-486, 1989.
Flegal, K.M., et al., "Prevalence and trends in obesity among US adults," JAMA, 2002, vol. 288, Issue 14, pp. 1-4, (1999-2000).
Fleischmann, D. and Hittmair, K., "Mathematical analysis of arterial enhancement and optimization of bolus geometry for CT angiography using the discrete Fourier transform," Journal of Computer Assisted Tomography, vol. 23, Issue 3, pp. 474-484 (May/Jun. 1999).
Fleischmann, D., "Contrast Medium Injection Technique," In: U. Joseph Schoepf: "Multidetector—Row CT of The Thorax," pp. 47-59 (Jan. 22, 2004).
Fleischmann, D., "Present and Future Trends in Multiple Detector-Row CT Applications; CT Angiography", European Radiology, vol. 12, Issue 2, Supplement 2, Jul. 2002, pp. s11-s15.
Gardiner, G. A, et al., "Selective Coronary Angiography Using a Power Injector," AJR Am J Roentgenol., vol. 146, Issue 4, pp. 831-833 (Apr. 1986).
Garrett, J. S., et al., "Measurement of cardiac output by cine computed tomography," The American Journal of Cardiology, vol. 56, Issue 10, pp. 657-661, 1985.

(56) References Cited

OTHER PUBLICATIONS

Gembicki, F.W., "Vector Optimization for Control with Performance and Parameter Sensitivity Indices," PhD Thesis Case Western Reserve University, 1974.
Gentilini A., et al., "A new paradigm for the closed-loop intraoperative administration of analgesics in humans," IEEE Transactions on Biomedical Engineering, vol. 49, Issue 4, pp. 289-299 (Apr. 2002).
Gerlowski L.E. and Jain R.K., "Physiologically Based Pharmacokinetic Modeling: Principles and Applications," Journal of Pharmaceutical Sciences, vol. 72, pp. 1104-1125, Oct. 1983.
Goss, J. E, et al., "Power injection of contrast media during percutaneous transluminal coronary artery angioplasty," Catheterization and Cardiovascular Diagnosis, vol. 16, Issue 3, pp. 195-198 (Mar. 1989).
Grant, S.C.D. et al., "Reduction of Radiation Exposure to the Cardiologist during Coronary Angiography by the Use of a Remotely Controlled Mechanical Pump for Injection of Contrast Medium," Catheterization and Cardiovascular Diagnosis, vol. 25, Issue 2, pp. 107-109 (Feb. 1992).
Hackstein, N. et al., "Glomerular Filtration Rate Measured by Using Triphasic Helical CT with a Two-Point Patlak Plot Technique," Radiology, vol. 230, Issue 1, pp. 221-226, Jan. 2004.
Hansen, P.C, Regularization tools: a MATLAB package for analysis and solution of discrete ill-posed problems, Numerical Algorithms, vol. 6, Issue 1, pp. 35, 1994.
Hansen, P.C., "The truncated SVD as a method for regularization," BIT Numerical Mathematics, vol. 27, Issue 4, pp. 334-555, 1987.
Harris P., H. D. "The Human Pulmonary Circulation," Edinburgh, Churchill Livingstone, (Appendix I), 1986.
Hayes, M., "Statistical Digital Signal Processing and Modeling", New York, New York, Wiley and Sons, 1996, pp. 154-177, (Prony's method).
Heiken; J.P. et al., "Dynamic Contrast-Enhanced CT of the Liver: Comparison of Contrast Medium Injection Rates and Uniphasic and Biphasic Injection Protocols", Radiology, May 1993, vol. 187, No. 2, pp. 327-331.
"Infus O.R. Multi-Drug Syringe Pump with Smart Labels," Bard MedSystems Division Inc., pp. 2693-2696 (2005).
International Preliminary Report on Patentability and International Search Report for International Patent Application No. PCT/US00/10842 dated May 22, 2001.
International Preliminary Report on Patentability and Wrtitten Opinion dated May 30, 2007 and International Search Report dated Sep. 25, 2006 for PCT App. No. PCT/US2005/042891.
International Preliminary Report on Patentability International Search Report, and Written Opinion for International Patent Application No. PCT/US2009/047168 dated Jan. 5, 2011.
International Preliminary Report on Patentability, International Search Report and Written Opinion for International Patent Application No. PCT/US2011/041802 dated Dec. 28, 2012.
"International Search Report and Written Opinion from PCT Application No. PCT/US2017/012801", dated May 9, 2017.
International Search Report for International Patent Application No. PCT/US96/15680 dated Jan. 28, 1997.
Ireland, M.A., et al., "Safety and Convenience of a Mechanical Injector Pump for Coronary Angiography," Catheterization and Cardiovascular Diagnosis, vol. 16, Issue 3, pp. 199-201 (1989).
Jacobs, J.R., "Algorithm for optimal linear model-based control with application to pharmacokinetic model-driven drug delivery," IEEE Transactions on Biomedical Engineering, vol. 37, Issue 1, pp. 107-109 (Jan. 1990).
Korosec, F.R., "Physical Principles of Phase-Contrast, Time-of-Flight, and Contrast-Enhanced MR Angiography," 41st Annual Meeting of American Association of Physicists in Medicine, Jul. 25-29, 1999.
Korosec, Frank, "Basic Principles of Phase-contrast, Time-of-flight, and Contrast-enhanced MR Angiography", 1999.
Krause, W, "Application of pharmacokinetics to computed tomography: injection rates and schemes: mono-, bi-, or multiphasic?," Investigative Radiology, vol. 31, Issue 2, pp. 91-100, Feb. 1996.

Krieger, R. A., "CO2-Power-Assisted Hand-Held Syringe: Better Visualization during Diagnostic and Interventional Angiography," Cathet Cardiovasc Diagn., vol. 19, Issue 2, pp. 123-128 (Feb. 1990).
Liebel-Flarsheim Company, "Angiomat 6000 Digital Injection System—Operator's Manual", Document No. 600950, Rev. 1, Jan 1990.
Mahnken, A. H., et al., "Determination of cardiac output with multislice spiral computed tomography: a validation study," Investigative Radiology, vol. 39, Issue 8, pp. 451-454, Aug. 2004.
Mahnken, A. H., et al., "Measurement of cardiac output from a test-bolus injection in multislice computed tomography," European Radiology, vol. 13, Issue 11, pp. 2498-504, 2003.
Mark V/Mark V Plus Injector Operation Manual KMP 805P Rev. B. Medrad, Inc, 1990.
McClellan, J.H., "Parametric Signal Modeling," Chapter 1 in Advanced Topics in Signal Processing, Pentice-Hall, Englewood Cliffs, NJ (1988).
MCT and MCT Plus Injection Systems Operation Manual KMP 810P, Medrad, Inc, 1991.
Neatpisarnvanit, C. and Boston, J.R., "Estimation of plasma insulin from plasma glucose", IEEE Transactions on Biomedical Engineering, vol. 49, Issue 11, pp. 1253-1259, 2002.
Non-Final office Action dated Mar. 12, 2013, in U.S. Appl. No. 13/655,525, John F. Kalafut et al., filed Oct. 19, 2012.
Office Action dated Jan. 3, 2014 in U.S. Appl. No. 11/691,823.
Office Actions dated Apr. 23, 2014, Apr. 26, 2013, Oct. 2, 2012 and dated Feb. 15, 2012, in U.S. Appl. No. 12/519,040, John F. Kalafut, filed Jun. 12, 2009.
Office Actions dated Nov. 5, 2012, Jun. 19, 2013, Dec. 12, 2014, in U.S. Appl. No. 13/186,983, John F. Kalafut et al., filed Jul. 20, 2011.
Office Actions dated Oct. 18, 2012, Jun. 17 2013, Mar. 5 2013, and Jul. 14, 2014 in U.S. Appl. No. 12/519,213, John F. Kalafut et al., filed Jun. 15, 2009.
Office Actions dated Sep. 17, 2012 and May 10, 2013, in U.S. Appl. No. 12/611,172, John F. Kalafut et al., filed Nov. 3, 2009.
Ostergaard, L., et al., "High resolution measurement of cerebral blood flow using intravascular tracer boluspassages. Part 1: Mathematical approach and statistical analysis," Magnetic Resonance in Medicine, vol. 36, Issue 5,pp. 715-725 (Nov. 1996).
Ostergaard, L., et al., "High resolution measurement of cerebral blood flow using intravascular tracer boluspassages. Part II: Experimental comparison and preliminary results," Magn Reson Med, vol. 36, Issue 5, pp. 726-736(Nov. 1996).
Parker, K.J., et al., "A Particulate Contrast Agent With Potential for Ultrasound Imaging of Liver," Ultrasound in Medicine & Biology, vol. 13, Issue 9, pp. 555-566 (Sep. 1987).
Rosen, B.R. et al., "Perfusion Imaging with NMR Contrast Agents," Magentic Resonance in Medicine, vol. 14, No. 2, pp. 249-265, May 1, 1990.
Sablayrolles, J-L, "Cardiac CT: Experience from Daily Practice", Advance CT, A GE Healthcare Publication. Aug. 2004.
Stevens, M.A., et al. "A Prospective Randomized Trial of Prevention Measures in Patients at High Risk for Contrast Nephropathy," J. of the ACC, vol. 33, Issue 2, pp. 403-411, Feb. 1999.
Supplementary European Search Report dated Apr. 15, 2011 in European Patent Application No. 07867951.1.
Supplementary European Search Report dated Aug. 19, 2010 in European Patent Application No. 05852259.0.
Supplementary European Search Report dated Dec. 9, 1998 in European Patent Application No. 96936079.0.
Supplementary European Search Report dated Jul. 23, 2013 in European Patent Application No. 08771789.8.
The European Search Report from EP14174725.3 dated May 8, 2015.
"The Solution for Your IV Formulas", Valley Lab. Inc., E-39-15, 3399, 3400, 2646.
Wada, D.R. and Ward, D.S., "Open loop control of multiple drug effects in anesthesia", IEEE Transactions on Biomedical Engineering, vol. 42, Issue 7, pp. 666-677, 1995.
Wada D.R. and Ward, D.S., "The hybrid model: a new pharmacokinetic model for computer-controlled infusion pumps", IEEE Transactions on Biomedical Engineering, 1994, vol. 41, Issue 2, pp. 134-142.

(56) References Cited

OTHER PUBLICATIONS

Yamashita, Y. et al., "Abdominal Helical CT: Evaluation of Optimal Doses of Intravenous Contrast Material—A Prospective Randomized Study," Radiology, vol. 216, Issue 3, pp. 718-723, Sep. 1, 2000.
International Preliminary Report on Patentability and Written Opinion for counterpart International Patent Application No. PCT/US2008/079160 dated Apr. 20, 2010.
"International Preliminary Report on Patentability for International Application No. PCT/US2017/020637", dated Sep. 13, 2018.
International Search Report and Written Opinion for counterpart International Patent Application No. PCT/US2008/079160 dated Dec. 4, 2008.
"International Search Report and Written Opinion from PCT Application No. PCT/US2017/020637", dated Jun. 23, 2017.
Morden Peter. et al.,, "The Role of Saline Flush Injection Rate in Displacement of CT Injectable Peripherally Inserted Central Catheter Tip During Power Injection of Contrast Material", AJR, Jan. 2014, 202, W13-W18.

SYSTEM AND METHOD FOR IMPROVED FLUID DELIVERY IN MULTI-FLUID INJECTOR SYSTEMS

CROSS REFERENCE TO RELATED APPLICATION

This application is a 371 national phase application of PCT International Application No. PCT/US2017/020637, filed Mar. 3, 2017, and claims the benefit of U.S. Provisional Patent Application No. 62/303,050, filed Mar. 3, 2016, the disclosure of which is hereby incorporated in its entirety by reference.

BACKGROUND

Field of the Technology

The present disclosure is directed to a system and method for reducing the occurrence of spikes in flow rates for a fluid delivery system having a fluid pumping device for delivery of two or more medical fluids in applications in medical diagnostic and therapeutic procedures.

Description of Related Art

In many medical diagnostic and therapeutic procedures, a physician or trained clinician injects fluid into a patient. For example, a physician may inject saline and/or an imaging contrast medium into a patient to help improve the visibility of internal body structures during one or more X-ray/CT imaging, MRI imaging, or other imaging procedure. To inject the saline and/or contrast medium, the clinician may use a manual injection syringe or may, alternatively, use a powered fluid injection system. A catheter is coupled to the manual injection syringe or injection device and is used to inject the saline and/or contrast medium into the patient (such as into a vessel in the patient's hand or arm). The contrast medium and saline are provided from separate sources, such as bags, bottles, or syringes, and, in certain cases, may be mixed together before injection into the patient. However, several problems may develop during use of certain capacitive pressure injection systems and syringes, including spikes in fluid flow rates, extravasation and/or infiltration, saline or contrast medium contamination during injection due to backflow of the fluids, real-time injection ratio inaccuracies, or kick-back in catheter tubes that are inserted into patients.

A. Extravasation and Infiltration

Extravasation and infiltration are often characterized as an accidental infusion of an injection fluid, such as a contrast medium (extravasation) or saline (infiltration), into tissue surrounding a blood vessel rather than into the blood vessel itself. Extravasation and infiltration can be caused, for example, by a fragile vascular system, valve disease, inaccurate needle placement, sudden changes in fluid flow, or patient movement resulting in the injected needle being pulled from the intended vessel or pushed through the wall of the vessel.

Additional extravasation and/or infiltration issues may occur when using both a contrast medium and saline for a procedure. As shown in FIG. 1, initially, no pressure is applied to the contrast medium 10 or saline 12, resulting in no flow through the fluid injector system. As shown in FIG. 2, pressure is then applied to the contrast medium 10 resulting in a pressure build up and initial backflow of contrast medium 10 into the saline 12 at point A. As a result, the flow rate of the contrast medium 10 may be reduced due to the effect of backflow and expansion in the contrast medium 10 bag or syringe and saline 12 bag or syringe due to the injection fluid pressure. Further, the saline 12 bag or syringe may expand depending on the particular capacitance of the saline 12 bag or syringe. As shown in FIG. 3, the flow rate and pressure of the contrast medium 10 may continue to increase, thereby stabilizing the pressure in the injector system. As shown in FIG. 4, due to the higher viscosity of the contrast medium 10, the pressure applied to the saline 12 must be increased further until resistance to the flow of the saline 12 drops and the saline 12 is directed into the contrast medium 10 flow at point B. Until the saline 12 reaches a pressure that is substantially similar to the contrast medium 10, the saline 12 stores pressure energy during the contrast medium 10 injection. When the saline 12 piston begins immediately after the contrast medium 10 injection stops, however, the flow rate of the saline 12 increases rapidly (higher than the flow rate programmed for the saline 12) due to the stored pressure energy (capacitance), sending an increased amount of saline 12 to mix with the contrast medium 10. This increased flow rate or flow spike can cause a rapid fluid acceleration in the catheter. The syringes or bags of the injector system will begin to deflate as the pressure within the syringes or bags decreases due to the uniform flow of contrast medium 10 and/or saline 12. The rapid increase in flow rate for the saline 12 creates a transition to turbulence that causes the resistance to slightly rise again, causing oscillations in the flow. Eventually, a stable flow rate is reached at a lower equilibrium pressure. However, due to the initial backflow and increased pressure in the fluid injector system, an increased injection pressure and/or flow rate of contrast medium 10 or saline 12 may be experienced.

B. Inaccurate Fluid Mixing Ratios

With further reference made to FIG. 1 and the injection process described above, also due to the initial backflow and increased pressure in the fluid injector system, accurate flow rates of contrast medium 10 and saline 12 are not always provided to the patient. Accurate flow rates of the contrast medium 10 and saline 12 may be achieved in average. However, for short periods of time until the system achieves steady state, the flow rates may be ramping, slowing down, peaking, and may not be particularly precise. In one scenario, the contrast medium 10 injection may be followed by the saline 12 injection, which causes a saline 12 overrate to the patient. In another scenario, a dual flow simultaneous injection of the contrast medium 10 and the saline 12 may cause inaccurate ratios of the contrast medium 10 and saline 12 until the system stabilizes.

An additional factor that may contribute to the problem of inaccurate fluid mixing ratios is the backflow of fluid that occurs in injections where the viscous contrast medium 10 is injected at a higher ratio than the less viscous saline 12. In such a scenario, before a uniform fluid flow is established, the fluid pressure of the more viscous contrast medium 10 that is injected at a higher ratio may act against the fluid pressure of the less viscous saline 12 that is injected at a lower ratio to force the contrast medium 10 to reverse the desired direction of flow. After injection, pressures equalize and the fluid injection system achieves a steady state operation where the contrast medium 10 and saline 12 are injected at a desired ratio. However, in small volume injections, steady state operation may not be achieved prior to the completion of the injection process and the fluid mixing ratio of contrast medium 10 and saline 12 being delivered to the patient may not be accurately achieved. Thus, even though a desired ratio of contrast medium 10 and saline 12 may be 80% contrast medium 10 to 20% saline 12, the actual ratio due to backflow of contrast medium 10 into the saline 12 may be higher. This problem is further compounded with an increase in injection pressure. In one particular example of a fluid injector system, the syringes are typically always pointing upwards and are used for multiple patients throughout an entire day. Therefore, contrast medium 10 may backflow into the saline syringe and sink to the bottom of the saline syringe. By the time multiple patients have been treated and multiple injections have been performed, the saline syringe may be substantially filled with contrast medium thereby contaminating and reducing the amount of the saline fluid 12.

C. Catheter Kickback and Rapid Movement

An additional complication with known multi-fluid injector systems is a kickback or rapid movement of the catheter in the patient's body as a result of the erratic flow of the contrast medium or saline. In many known multi-fluid injector systems, the saline and contrast medium tubing is connected to a catheter that is used for injecting the fluids into the patient. However, due to the backflow of the saline and/or contrast medium and the rapid acceleration of contrast medium or saline into the fluid line of the multi-fluid injector system during fluid transitions, the catheter may at least partially kick-back or otherwise change position within the patient vasculature. Fluid accelerations may be caused by nozzle effects in the catheter and rapid increases in flow rate during contrast medium-to-saline transitions. The nozzle on the catheter may accelerate the fluid from a lower flow rate in the tubing of the catheter to an increased flow rate exiting the catheter. The transition from a contrast medium injection to a saline injection causes a rapid flow rate increase. The force imparted to the catheter may cause undesired movement of the catheter. Complications related to extravasation and infiltration, inaccurate fluid mixing ratios, and catheter kickback and rapid movement may include unnecessary pain and discomfort to the patient. There is a current need for a system that provides accurate flow rates of saline and/or contrast medium to a patient, thereby reducing the risk of extravasation and/or infiltration. There is also a current need for a catheter design that reduces kickback and rapid movement of the catheter during injection of a fluid into a patient's blood vessel.

BRIEF SUMMARY

In view of the foregoing, a need exists for an improved fluid delivery system for fluid delivery applications in medical diagnostic and therapeutic procedures. There is an additional need in the medical field for a fluid delivery system that provides a more precise and efficient flow rate or ratio of fluids during initial injection procedures compared to existing fluid delivery systems. Existing fluid delivery systems do not always provide accurate flow rates or mixing ratios of the desired fluids resulting in the risk of extravasation and/or infiltration. There is a current need for a fluid delivery system that allows an individual to quickly and accurately provide the necessary flow rate or ratio of fluids to a patient.

In one example, a method of maintaining a substantially uniform overall flow rate during a sequential delivery of at least two fluids to a patient's blood vessel includes delivering at least a first fluid into the patient's blood vessel at a first flow rate, delivering at least a second fluid into the patient's blood vessel at a second flow rate, and adjusting at least one of a first flow profile of the first flow rate and a second flow profile of the second flow rate to dampen a transient increase in the overall flow rate during a transition between delivering one of the first fluid and the second fluid to delivering the other of the first fluid and the second fluid.

In another example, the method further includes delaying the delivery of one of the first fluid and the second fluid until the other of the first fluid and the second fluid reaches a predetermined flow rate. The method may include adjusting one of the first flow rate and the second flow rate using a controller based on the other of the first flow rate and the second flow rate. The method may include pressurizing the first fluid using a check valve to a predetermined pressure before delivering the first fluid. The method may include pressurizing the second fluid using a check valve to a predetermined pressure before delivering the second fluid. The method may include pressurizing the first fluid and the second fluid using separate check valves to a first predetermined pressure and a second predetermined pressure, respectively, before delivering the first fluid and the second fluid.

The method may include over-delivering a predetermined volume of at least one of the first fluid and the second fluid during the delivery of at least one of the first fluid and the second fluid. The method may include diluting one of the first fluid and the second fluid with a predetermined volume of the other of the first fluid and the second fluid.

The method may include providing a multi-fluid injection system including a first syringe for receiving the first fluid and a first plunger movable within a barrel of the first syringe to pressurize the first fluid for delivery to the patient's blood vessel, and a second syringe for receiving the second fluid and a second plunger movable within a barrel of the second syringe to pressurize the second fluid for delivery to the patient's blood vessel, and reducing a capacitance of at least one of the first syringe and the second syringe to prevent backflow of at least one of the second fluid into the first syringe and the first fluid into the second syringe. The method may include providing a pressure jacket around an outer circumference of at least one of the first syringe and the second syringe to reduce swelling of at least one of the first syringe and the second syringe under pressure.

The method may include providing a multi-fluid injection system including a first syringe for receiving the first fluid and a first plunger movable within a barrel of the first syringe to pressurize the first fluid for delivery to the patient's blood vessel, and a second syringe for receiving the second fluid and a second plunger movable within a barrel of the second syringe to pressurize the second fluid for delivery to the patient's blood vessel, and wherein at least one of the first syringe and the second syringe includes a reduced inside diameter to correspond to a desired flow rate. The method may include providing an obstruction member within at least one of the first syringe and the second syringe to reduce the inner diameter of at least one of the first syringe and the second syringe.

The method may include providing a multi-fluid injection system including a first syringe for receiving the first fluid and a first plunger movable within a barrel of the first syringe to pressurize the first fluid for delivery to the patient's blood vessel, and a second syringe for receiving the second fluid and a second plunger movable within a barrel of the second syringe to pressurize the second fluid for delivery to the patient's blood vessel, and providing an external restriction member on an outer circumference of at least one of the first syringe and the second syringe; and adjusting an inner diameter of the external restriction member to adjust a permitted swelling of at least one of the first syringe and the second syringe.

The method may include controlling one of the first flow rate and the second flow rate using an equalizing flow valve based on the other of the first flow rate and the second flow rate. The method may include adjusting at least one of the first flow rate and the second flow rate before delivery of at least one of the first fluid and the second fluid based on at least one of known operating fluid pressure and capacitance of a multi-fluid injection system used to deliver the first fluid and the second fluid. The method may include increasing a transition time between delivering one of the first fluid and the second fluid and delivering the other of first fluid and the second fluid.

In another example, a controller for a multi-fluid injection system configured to maintain an overall flow rate during a sequential delivery of at least two fluids to a patient's blood vessel, the system includes a processor configured to control the multi-fluid injection system to: deliver at least a first fluid into the patient's blood vessel at a first flow rate, deliver at least a second fluid into the patient's blood vessel at a second flow rate, and adjust at least one of a first flow profile of the first flow rate and a second flow profile of the second flow rate to dampen a transient increase in the overall flow rate during a transition between delivering one of the first fluid and the second fluid to delivering the other of the first fluid and the second fluid.

In another example, the processor is further configured to control the multi-fluid injection system to increase a transition time between delivering one of the first fluid and the second fluid and delivering the other of the first fluid and the second fluid. The processor may also be further configured to control the multi-fluid injection system to delay the delivery of one of the first fluid and the second fluid until the other of the first fluid and the second fluid reaches a predetermined flow rate. The processor may also be further configured to control the multi-fluid injection system to over-deliver a predetermined volume of at least one of the first fluid and the second fluid during delivery of at least one of the first fluid and the second fluid.

Further examples will now be described in the following numbered clauses.

Clause 1: A method of maintaining an overall flow rate during a sequential delivery of at least two fluids to a patient's blood vessel, the method comprising: delivering at least a first fluid into the patient's blood vessel at a first flow rate; delivering at least a second fluid into the patient's blood vessel at a second flow rate; and adjusting at least one of a first flow profile of the first flow rate and a second flow profile of the second flow rate to dampen a transient increase in the overall flow rate during a transition between delivering one of the first fluid and the second fluid to delivering the other of the first fluid and the second fluid.

Clause 2: The method of Clause 1, wherein adjusting at least one of the first flow profile of the first flow rate and a second flow profile of the second flow rate comprises delaying the delivery of one of the first fluid and the second fluid until the other of the first fluid and the second fluid reaches a predetermined flow rate.

Clause 3: The method of Clause 1 or Clause 2, wherein adjusting at least one of the first flow profile of the first flow rate and a second flow profile of the second flow rate comprises adjusting one of the first flow rate and the second flow rate using a controller based on the other of the first flow rate and the second flow rate.

Clause 4: The method of any of Clauses 1-3, further comprising pressurizing the first fluid using a check valve to a predetermined pressure before delivering the first fluid.

Clause 5: The method of any of Clauses 1-4, further comprising pressurizing the second fluid using a check valve to a predetermined pressure before delivering the second fluid.

Clause 6: The method of any of Clauses 1-5, further comprising pressurizing the first fluid and the second fluid using separate check valves to a first predetermined pressure and a second predetermined pressure, respectively, before delivering the first fluid and the second fluid.

Clause 7: The method of any of Clauses 1-6, wherein adjusting at least one of the first flow profile of the first flow rate and a second flow profile of the second flow rate comprises over-delivering a predetermined volume of at least one of the first fluid and the second fluid during the delivery of at least one of the first fluid and the second fluid.

Clause 8: The method of any of Clauses 1-7, further comprising diluting one of the first fluid and the second fluid with a predetermined volume of the other of the first fluid and the second fluid.

Clause 9: The method of any of Clauses 1-8, further comprising: providing a multi-fluid injection system comprising: a first syringe for receiving the first fluid and a first plunger movable within a barrel of the first syringe to pressurize the first fluid for delivery to the patient's blood vessel; and a second syringe for receiving the second fluid and a second plunger movable within a barrel of the second syringe to pressurize the second fluid for delivery to the patient's blood vessel; and reducing a capacitance of at least one of the first syringe and the second syringe to prevent backflow of at least one of the second fluid into the first syringe and the first fluid into the second syringe.

Clause 10: The method of Clause 9, further comprising providing a pressure jacket around an outer circumference of at least one of the first syringe and the second syringe to reduce swelling of at least one of the first syringe and the second syringe under pressure.

Clause 11: The method of any of Clauses 1-10, further comprising: providing a multi-fluid injection system comprising: a first syringe for receiving the first fluid and a first plunger movable within a barrel of the first syringe to pressurize the first fluid for delivery to the patient's blood vessel; and a second syringe for receiving the second fluid and a second plunger movable within a barrel of the second syringe to pressurize the second fluid for delivery to the patient's blood vessel; and wherein at least one of the first syringe and the second syringe includes a reduced inside diameter to correspond to a desired flow rate.

Clause 12: The method of Clause 11, further comprising providing an obstruction member within at least one of the first syringe and the second syringe to reduce the inner diameter of at least one of the first syringe and the second syringe.

Clause 13: The method of any of Clauses 1-12, further comprising: providing a multi-fluid injection system comprising: a first syringe for receiving the first fluid and a first plunger movable within a barrel of the first syringe to pressurize the first fluid for delivery to the patient's blood vessel; and a second syringe for receiving the second fluid and a second plunger movable within a barrel of the second syringe to pressurize the second fluid for delivery to the patient's blood vessel; providing an external restriction member on an outer circumference of at least one of the first syringe and the second syringe; and adjusting an inner diameter of the external restriction member to adjust a permitted swelling of at least one of the first syringe and the second syringe.

Clause 14: The method of any of Clauses 1-13, wherein adjusting at least one of the first flow profile of the first flow rate and a second flow profile of the second flow rate comprises controlling one of the first flow rate and the second flow rate using an equalizing flow valve based on the other of the first flow rate and the second flow rate.

Clause 15: The method of any of Clauses 1-14, wherein adjusting at least one of the first flow profile of the first flow rate and a second flow profile of the second flow rate comprises adjusting at least one of the first flow rate and the second flow rate before delivery of at least one of the first fluid and the second fluid based on at least one of known operating fluid pressure and capacitance of a multi-fluid injection system used to deliver the first fluid and the second fluid.

Clause 16: The method of any of Clauses 1-15, wherein adjusting at least one of the first flow profile of the first flow rate and a second flow profile of the second flow rate comprises increasing a transition time between delivering one of the first fluid and the second fluid and delivering the other of first fluid and the second fluid.

Clause 17: A multi-fluid injection system configured to maintain an overall flow rate during a sequential delivery of at least two fluids to a patient's blood vessel, the system comprising: a processor configured to control the multi-fluid injection system to: deliver at least a first fluid into the patient's blood vessel at a first flow rate; deliver at least a second fluid into the patient's blood vessel at a second flow rate; and adjust at least one of a first flow profile of the first flow rate and a second flow profile of the second flow rate to dampen a transient increase in the overall flow rate during a transition between delivering one of the first fluid and the second fluid to delivering the other of the first fluid and the second fluid.

Clause 18: The controller of Clause 17, wherein the processor is further configured to control the multi-fluid injection system to increase a transition time between delivering one of the first fluid and the second fluid and delivering the other of the first fluid and the second fluid.

Clause 19: The controller as claimed in Clause 17 or Clause 18, wherein the processor is further configured to control the multi-fluid injection system to delay the delivery of one of the first fluid and the second fluid until the other of the first fluid and the second fluid reaches a predetermined flow rate.

Clause 20: The controller as claimed in any of Clauses 17-19, wherein the processor is further configured to control the multi-fluid injection system to over-deliver a predetermined volume of at least one of the first fluid and the second fluid during delivery of at least one of the first fluid and the second fluid.

These and other features and characteristics of the fluid injection system, as well as the methods of operation and functions of the related elements of structures and the combination of parts and economies of manufacture, will become more apparent upon consideration of the following description and the appended claim with reference to the accompanying drawings, all of which form a part of this specification, wherein like reference numerals designate corresponding parts in the various figures. It is to be expressly understood, however, that the drawings are for the purpose of illustration and description only, and are not intended as a definition of the limits of the disclosure. As used in the specification and the claim, the singular form of "a", "an", and "the" include plural referents unless the context clearly dictates otherwise.

DESCRIPTION OF THE DISCLOSURE

Figure 1:
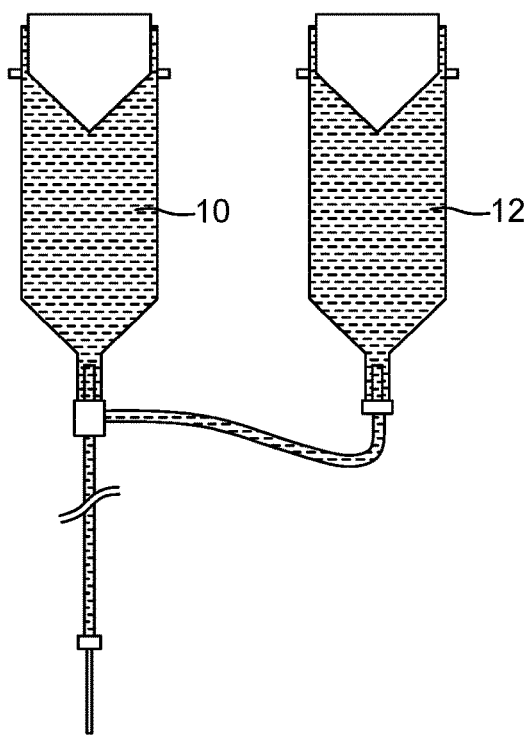
FIGS. 1-4 are schematic views depicting known methods of injecting a first fluid and a second fluid to a patient using a fluid injection system.
Figure 2:
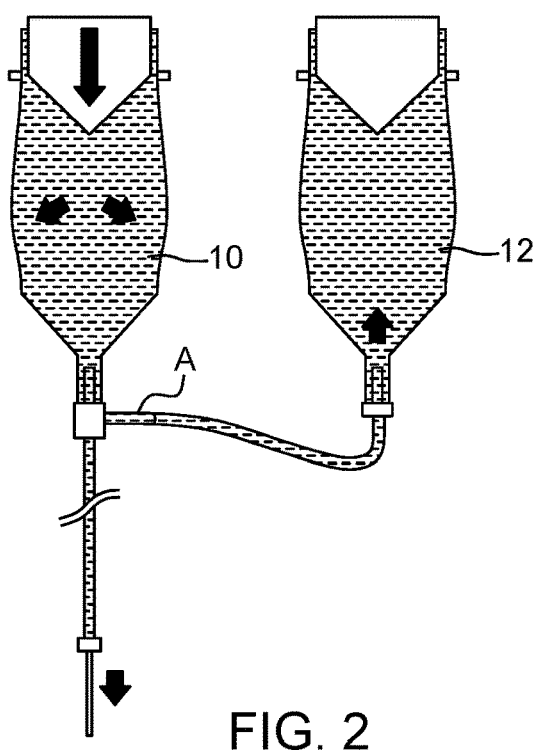
Figure 3:
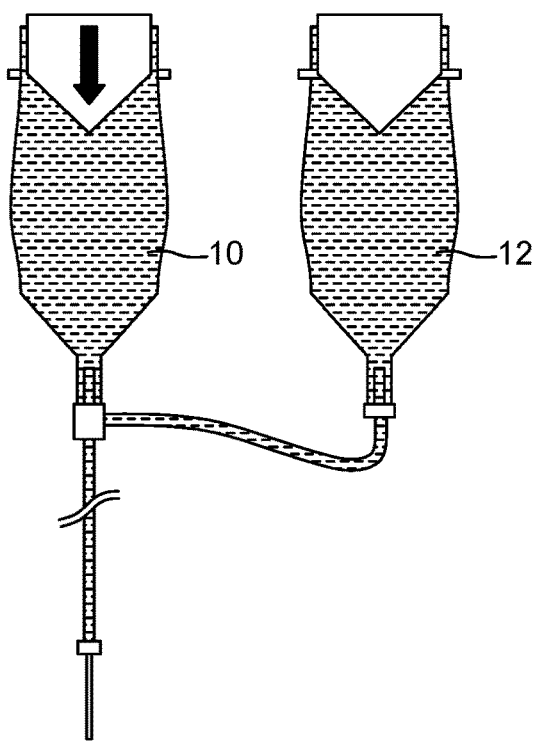
Figure 4:
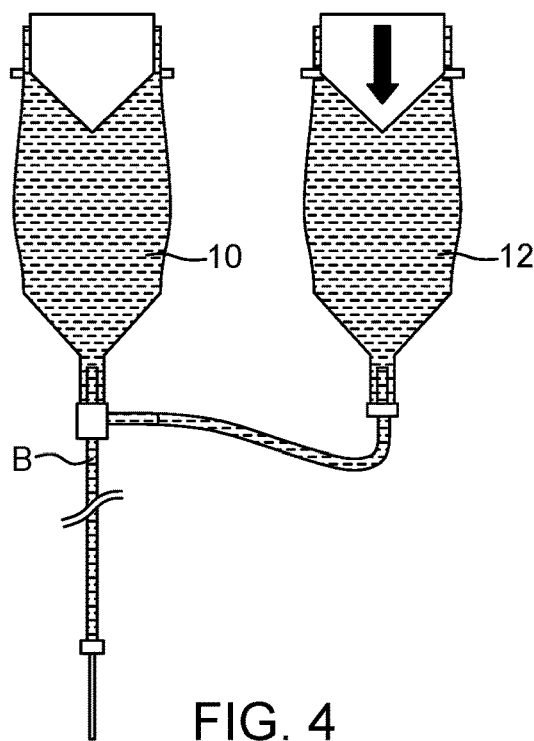

For the purposes of the description hereinafter, spatial orientation terms, if used, shall relate to the referenced example as it is oriented in the accompanying drawings, figures, or otherwise described in the following detailed description. However, it is to be understood that the examples described hereinafter may assume many alternative variations and examples. It is also to be understood that the specific systems illustrated in the accompanying drawings, figures, and described herein are simply exemplary and should not be considered as limiting.

Referring to the drawings in which like reference characters refer to like parts throughout the several views thereof, several systems and methods are provided for reducing incidences of infiltration and/or extravasation, reducing the occurrence of spikes or sudden changes in fluid flow rates during an injection procedure, ensuring accurate flow rates and mixing ratios of fluids are delivered to the patient, and reducing kickback and rapid movement of a catheter during a transition from one injected fluid to another fluid. In a typical multi-fluid injection procedure, an injection fluid, such as a contrast medium, is delivered from a contrast medium source to the patient using a powered or manual injector. The injected contrast medium is delivered to a desired site in a patient's body through a catheter inserted into the patient's body, such as the arm. Once the contrast medium is delivered to the desired site, the area is imaged using a conventional imaging technique, such as computed tomography (CT), angiography imagining, magnetic resonance imaging (MRI), or other imaging or scanning technique. The contrast medium becomes clearly visible against the background of the surrounding tissue. However because the contrast medium may comprise toxic substances, it is desirable to reduce contrast dosing to the patient, while maintaining an effective contrast amount necessary for accurate imaging. By supplementing an overall contrast medium delivery procedure with saline, the saline flushes the contrast medium to the area of interest and additional hydration of the patient occurs automatically and aids the body in removing the contrast medium. In addition to improved patient comfort level and less toxicity, introduction of saline at clinically significant pressures and flow rates also allows higher flow rates to be achieved at lower pressure settings on the injector.

Figure 30:
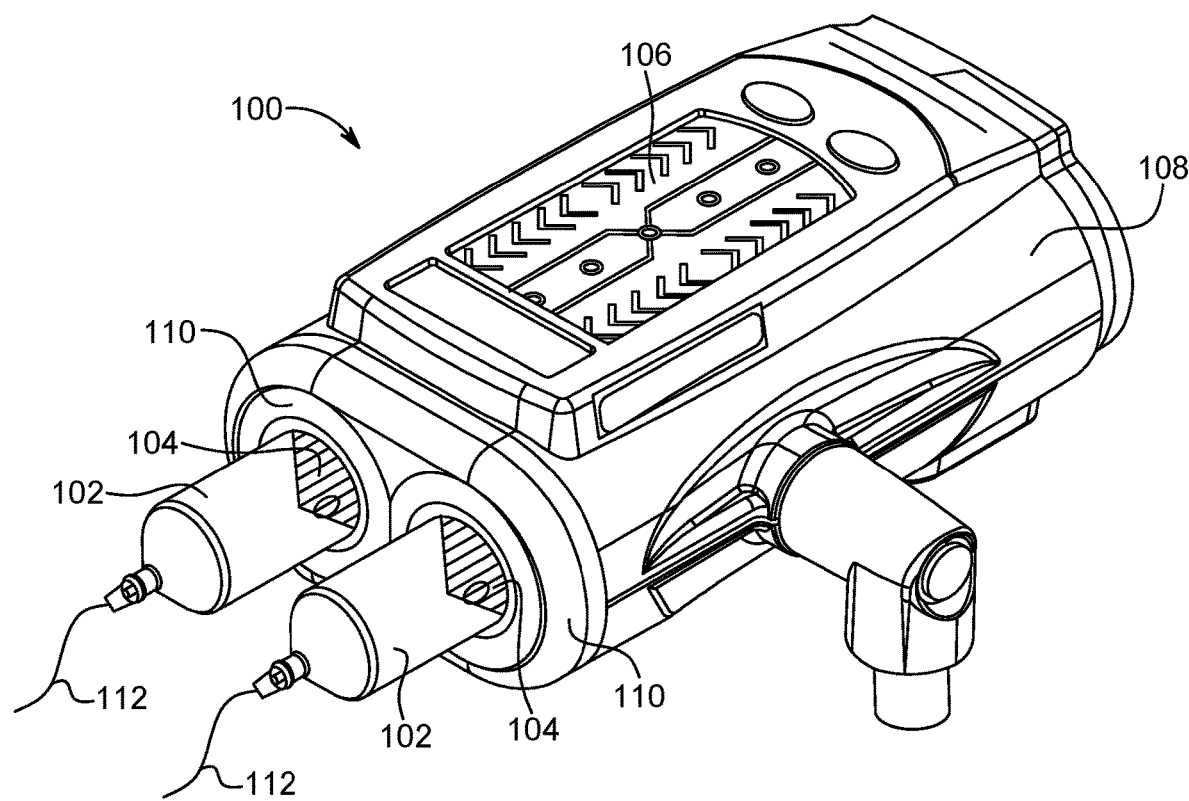
FIG. 30 is a perspective view of a multi-fluid injection system according to an example of the present disclosure.

In one example, as shown in FIG. 30, a fluid injector 100 (hereinafter referred to as "injector 100"), such as an automated or powered fluid injector, is adapted to interface with and actuate at least one syringe 102, each of which may be independently filled with a medical fluid, such as contrast medium, saline solution, or any desired medical fluid. The injector 100 may be used during a medical procedure as described herein to inject the medical fluid into the body of a patient by driving a plunger 104 of the at least one syringe 102 with at least one piston (not shown). The injector 100 may be a multi-syringe injector, wherein several syringes 102 may be oriented in a side-by-side or other arrangement and include plungers 104 separately actuated by respective pistons associated with the injector 100. In examples with two syringes arranged in a side-by-side relationship and filled with two different medical fluids, the injector 100 may deliver fluid from one or both of the syringes 102. The injector 100 has a control mechanism 106 for controlling operation of at least one operating parameter of injector 100, such as the injection pressure, volume, and/or flow rate of fluid delivered from at least one of the syringes 102.

The injector 100 has a housing 108 formed from a suitable structural material, such as plastic or metal, that encloses various components for delivering fluid from the syringes 102. The housing 108 may have various shapes and sizes depending on a desired application. The injector 100 includes at least one syringe port 110 for connecting the at least one syringe 102 to respective piston elements. In some examples, the at least one syringe 102 includes at least one syringe retaining member for retaining the syringe 102 within a syringe port 110 of the injector 100. The at least one syringe retaining member operatively engages a locking mechanism provided on or in the syringe port 110 of the injector 100 to facilitate loading and/or removal of the syringe 102 to and from the injector 100.

Figure 33:
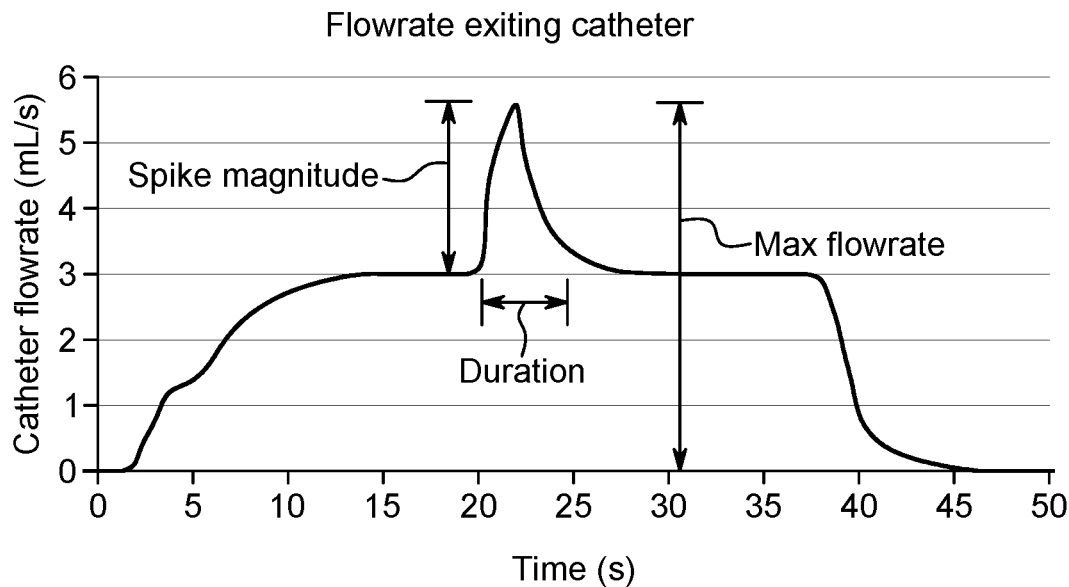
FIG. 33 is an annotated graph depicting an overall flow rate of fluid exiting a catheter with a contrast medium to saline transition.

At least one fluid path set 112 may be fluidly connected with the at least one syringe 102 for delivering medical fluid from the at least one syringe 102 to a catheter, needle, or other fluid delivery device (not shown) inserted into a patient at a vascular access site. Fluid flow from the at least one syringe 102 may be regulated by a fluid control module. The fluid control module may operate various pistons, valves, and/or flow regulating structures to regulate the delivery of the medical fluid, such as saline solution and contrast medium, to the patient based on user selected injection parameters, such as injection flow rate, duration, total injection volume, and/or ratio of contrast medium and saline. An example of a suitable front-loading fluid injector 100 that may be modified for use with the above-described system including at least one syringe 102 and at least one syringe interface loading and releasable retaining of the at least one syringe 102 with the fluid injector 100 described herein with reference to FIG. 33 is disclosed in U.S. Pat. No. 5,383,858 to Reilly et al.; U.S. Pat. No. 9,173,995 to Tucker et al.; and U.S. Pat. No. 9,199,033 to Cowen et al., each of which are incorporated herein by reference in their entirety. Another example of a multi-fluid delivery systems that may be modified for use with the present system is found in U.S. Pat. No. 7,553,294 to Lazzaro et al.; U.S. Pat. No. 7,666,169 to Cowen et al.; International Patent Publication No. WO 2012/155035; and United States Patent Application Publication No. 2014/0027009 to Riley et al.; the disclosures of which are incorporated herein by reference.

To enable effective simultaneous flow delivery of first and second injection fluids, such as contrast and saline, substantially equal pressure must be present in each delivery line. In a powered injection systems described herein, in a dual flow mode it is desirable to actuate the plunger elements substantially simultaneously in simultaneous flow delivery applications to equalize the pressure in each line. Alternatively, in a single flow mode, one plunger element is actuated to deliver the desired fluid while the other plunger element is held in place. If the injector is operated with differential pressure in each delivery line of the fluid path set, fluid in the lower pressure line may be stopped or reversed until sufficient pressure is achieved in the lower pressure line to enable flow in a desired direction. This time delay could reduce the image quality. The fluid in the lower pressure side may also begin to store fluid pressure energy against the fluid in the higher pressure line. As the stored fluid pressure energy in the lower pressure side continues to build, the lower pressure will eventually achieve the same pressure as the higher pressure fluid as it exits into the catheter tubing. Due to the stored fluid pressure energy in the lower pressure side, the flow rate of the lower pressure fluid can rapidly accelerate into the catheter tubing, particularly when the pressure in the high pressure fluid is reduced.

Figure 31:
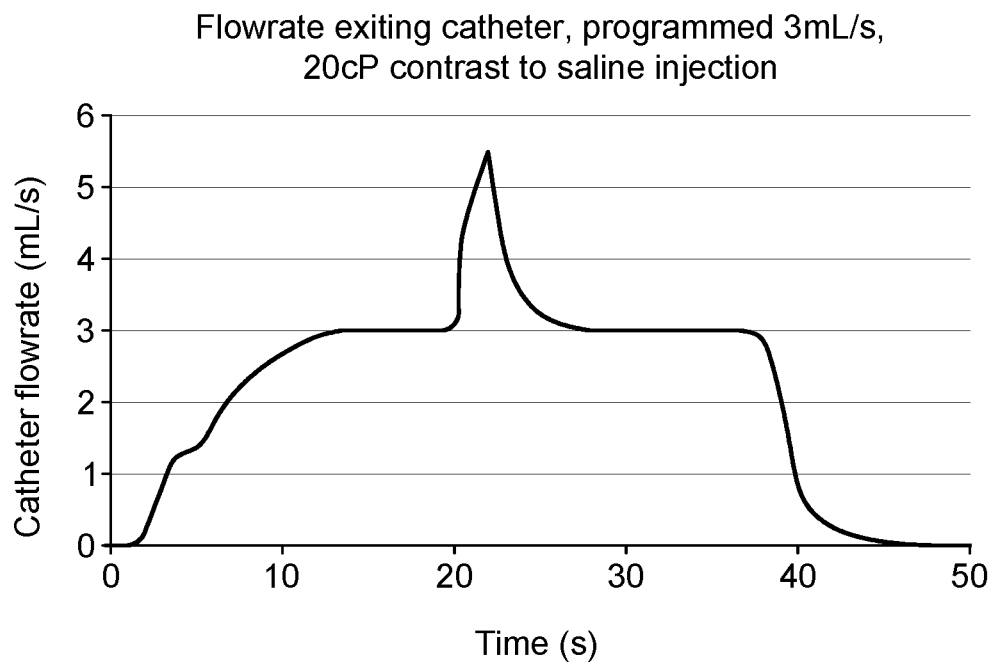
FIG. 31 is a graph depicting an overall flow rate of fluid exiting a catheter with a contrast medium to saline transition.

As shown in FIGS. 31 and 33, when delivering contrast medium and, subsequently, saline solution to a patient's blood vessel, a spike or sudden increase in an overall flow rate of fluid exiting the catheter may be experienced during a flow transition between the contrast medium and the saline. In one example, an overall flow rate through the catheter is understood to be the combined flow rate of the first fluid (in one example, saline solution) and the second fluid (in one example, contrast medium) exiting from the catheter. In one example, in which there is no flow of contrast medium through the catheter, the overall flow rate is equal to the flow rate of the saline solution. In another example, in which there is no flow of saline solution through the catheter, the overall flow rate is equal to the flow rate of the contrast medium. In another example, in which there is flow of saline solution and contrast medium through the catheter, the overall flow rate is equal to the combined flow rates of the saline solution and the contrast medium. Therefore, a fluid system may have a first flow rate corresponding to the flow rate of the first fluid, a second flow rate corresponding to the flow rate of the second fluid, and an overall flow rate corresponding to the combination of flow rates of the first and second fluids. As shown in FIGS. 31 and 33, as the contrast medium is initially directed through the catheter, the overall flow rate of the system equals the flow rate of the contrast medium and gradually increases to a desired steady-state flow rate. In FIG. 33, in one example, the desired overall flow rate exiting the catheter is 3 mL/s. Once a sufficient volume of contrast medium has been directed through the catheter and into the patient's blood vessel, a volume of saline solution is subsequently directed through the catheter to flush the contrast into the patient. As the delivery of the more viscous contrast medium transitions to the delivery of less viscous saline solution from the catheter, a sudden spike or increase in the overall flow rate is experienced in the system. As shown in FIG. 33, this spike or increase in the overall flow rate lasts for a specified duration and increases the overall flow rate of the system to a flow rate greater than the desired overall flow rate. As shown, the overall flow rate may increase to 5.5 mL/s, which is 2.5 mL/s higher than desired for the injection protocol. Therefore, it is an object of the present disclosure to dampen the sudden spike or increase in the overall flow rate exiting the catheter, for example by reducing the height of the spike and/or the duration of the spike, by adjusting a flow profile of the saline solution and/or the flow profile of the contrast medium during a transition between the delivery of the contrast medium to the delivery of the saline solution. Several different methods and arrangements for dampening the increase in overall flow rate exiting the catheter and reducing the duration of the increased overall flow rate are described below.

Figure 32:
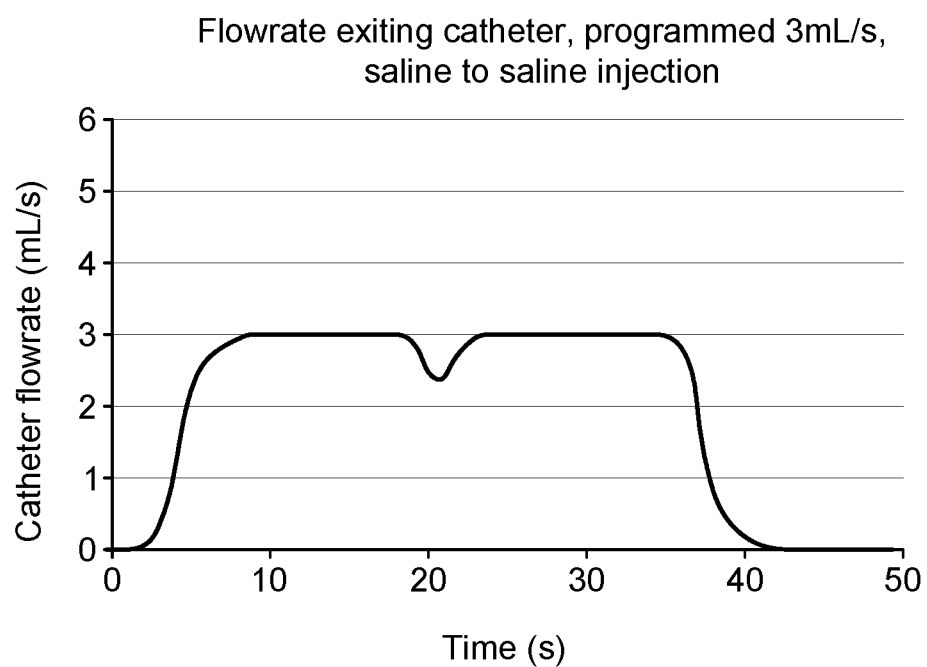
FIG. 32 is a graph depicting an overall flow rate of fluid exiting a catheter with a saline to saline transition.
Figure 34:
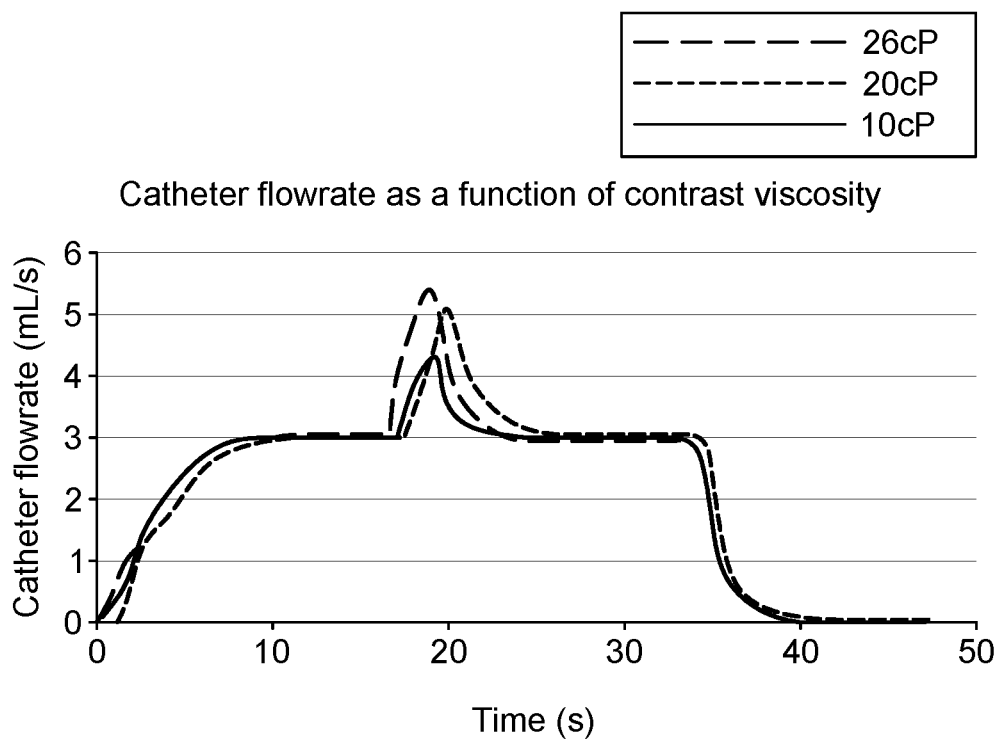
FIG. 34 is a graph depicting several different overall catheter flowrates of varying contrast medium viscosity.
Figure 35:
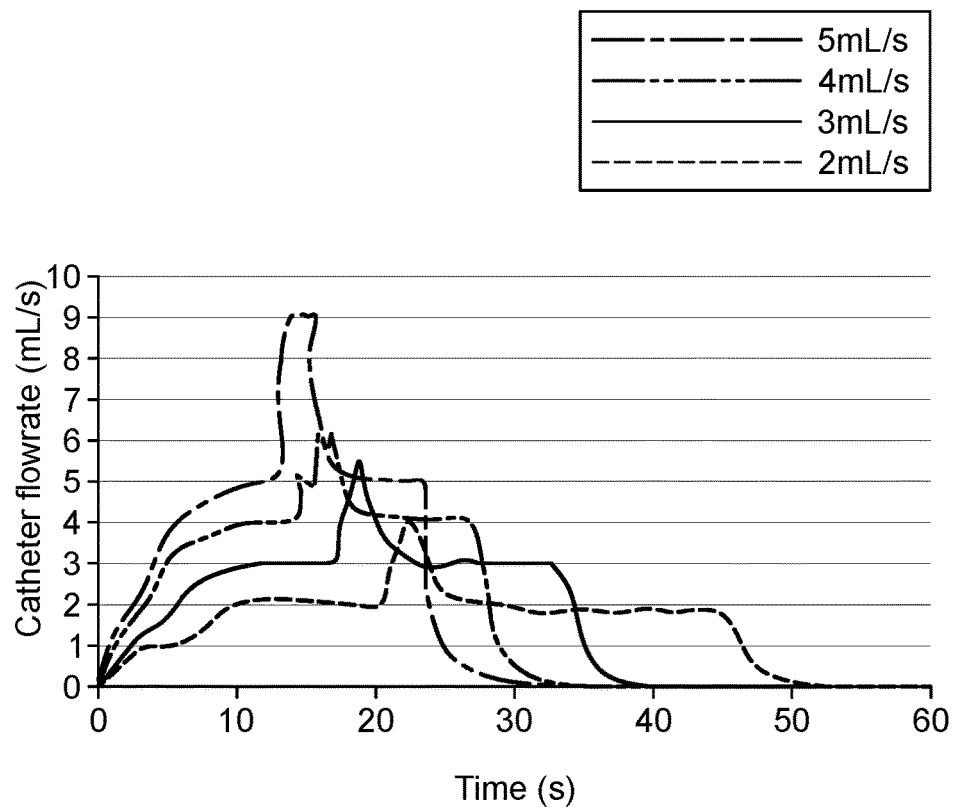
FIG. 35 is a graph depicting several different overall catheter flowrates.

As shown in FIG. 32, in a system delivering only saline solution to a patient, there is no sudden spike or increase observed in the overall flow rate exiting the catheter when switching from one saline syringe to another. In fact, the system may experience a slight temporary decrease in the overall flow rate exiting the catheter. As shown in FIG. 34, the difference in viscosity of the contrast medium used in the system compared to that of the saline (Δ-Viscosity) may also affect the severity of the sudden spike or increase in the overall flow rate exiting the catheter. For example, a contrast medium with a higher viscosity (e.g., 26 cP) may contribute to a larger spike or increase in the overall flow rate exiting from the catheter than a contrast medium with a lower viscosity (e.g., 10 cP). As shown in FIG. 35, the desired overall flow rate of the fluid exiting from the catheter may also affect the severity of the sudden spike or increase in the overall flow rate exiting the catheter. For example, a higher desired overall flow rate (e.g., 5 mL/s) may contribute to a larger spike or increase in the overall flow rate exiting from the catheter than a lower desired overall flow rate (e.g., 2 mL/s).

Further, the fluid mixing ratio of contrast medium-to-saline may become inaccurate due to the stored fluid pressure energy in the lower pressure saline syringe or line. The contrast medium may be injected at a significantly higher ratio relative to saline, such as 80% contrast medium to 20% saline injection protocol. The flow reversal may be exacerbated at high injection pressures. In small dosage injections at a high injection pressure, flow reversal may effectively stop the delivery of saline such that up to 100% contrast medium is injected, rather than the desired 80% contrast medium to 20% saline ratio. Similar inaccuracies may occur at various other injection protocols, including, but not limited to 20% contrast medium to 80% saline ratio.

The above-described situation of flow reversal during powered injections at high contrast medium-to-saline ratio may occur at least in part due to injection system capacitance. Total system capacitance (also referred to as compliance or the ability to store a fluid volume and/or hydraulic energy) represents the amount of suppressed fluid (i.e., backflow volume) that is captured in the swelling of the fluid injector system components or compression of fluid injector system components, such as the fluid lines and/or syringe(s) due to pressure applied to a medical fluid during an injection process. Total system capacitance is inherent to each fluid injection system and depends on a plurality of factors, including injector construction, mechanical properties of materials used to construct the syringe, plunger, pressure jacket surrounding the syringe, fluid lines delivering the contrast medium and saline to a flow mixing device, size or surface area of the syringe, plunger, pressure jacket, compression or deflection of syringe injector components, etc. The amount of back or reverse flow increases when the relative speed difference between the two plungers is large, the simultaneous fluid flow is through a small restriction, the speed of the total fluid injection is large, and/or the viscosity of the fluid is high. The back or reverse flow can prevent different ratios of simultaneously delivered fluid from occurring in certain injections, which can be a detriment for two-syringe type fluid injector systems.

In general, capacitance is directly correlative to injection pressure and inversely correlative to volume of contrast medium and saline in the syringes. For example, in one example, capacitance during an injection at 1200 psi with 150 mL of contrast medium and saline remaining in certain medical injector syringes is around 10 mL. In another example, the capacitance volume can be from about 5 mL to about 9 mL. Capacitance is also a function of the ratio at which the first and second injection fluids, such as contrast and saline, are injected. At a 50%-50% ratio, where contrast and saline are injected in equal amounts, backflow volume is minimized because the capacitance on the contrast medium side is equal to the capacitance on the saline side of the fluid injection system such that substantially equal pressures are present in each delivery line. Backflow may occur in situations where first and second injection fluids are delivered through long fluid conduits. However, as the injection ratio of contrast and saline changes, backflow volume increases corresponding to the increase in the ratio.

Figure 36A:
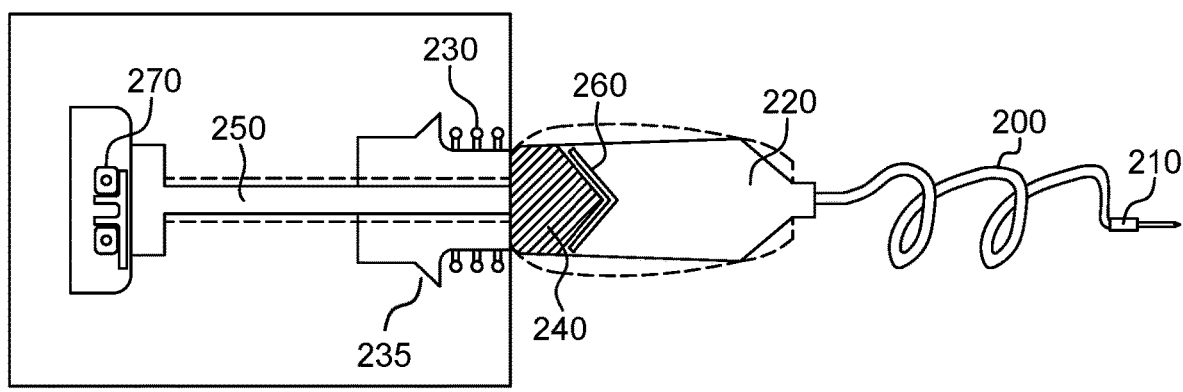
FIG. 36A is a schematic of a multi-fluid injection system according to an example of the present disclosure.
Figure 36B:
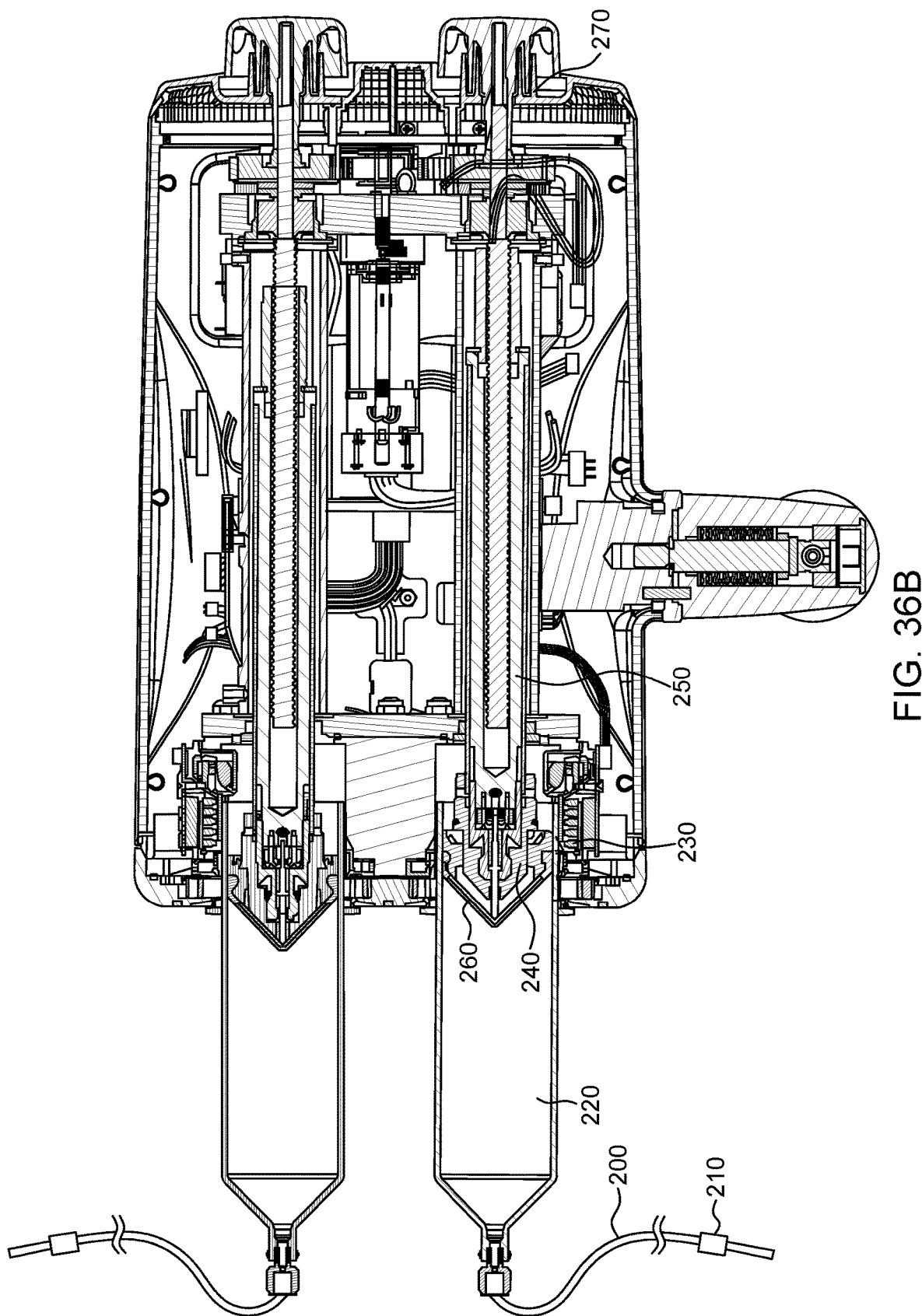
FIG. 36B is a cross-sectional view of the multi-fluid injection system of FIG. 30.

With reference to FIG. 36, capacitance in a particular injector system can occur in several different locations during an injection procedure of the system. In particular, in one example, the catheter tubing 200 of the system may experience swelling and/or compression during an injection procedure, which can affect the flow rates of the fluids through the tubing 200. In another example, the catheter 210 itself may experience swelling and/or compression during an injection procedure, which can affect the flow rate of the fluid exiting the catheter 210. In another example, the syringe 220 of the injector system may experience swelling and/or compression during an injection procedure. The swelling of the syringe 220 may occur in the form of radial expansion and/or axial expansion of the syringe 220. In another example, the syringe interface 230 may experience swelling and/or compression during an injection procedure. The syringe interface 230 is the connection between the syringe 220 and the injector system. In one example, the syringe interface 230 may include locking mechanisms, O-rings or other sealing members that can experience swelling and/or compression during the injection procedure. In another example, locking features 235 on the syringe, such as flanges or lugs may compress or bend under the applied pressure. In another example, a piston head 240 in the injector system may experience swelling and/or compression during an injection procedure, for example if there is mechanical play between the piston head 240 and the corresponding syringe plunger. Due to the forces exerted by and on the piston head 240, compression forces may create swelling in the piston head 240. In another example, the piston 250 may experience bending, torqueing, swelling and/or compression during an injection procedure. Due to the forces exerted by and on the piston 250, compression forces may create swelling in the piston 250 and corresponding reduction in piston length. In another example where a polymeric cover 260 is provided on piston head 240 or syringe plunger assembly, the polymeric cover 260 may experience swelling and/or compression during an injection procedure. In another example, a strain gauge cap 270 positioned in the injector system on an end of piston 250 may experience swelling and/or compression during an injection procedure. Although the strain gauge cap 270 is configured to stretch to measure strain in piston 250, the injection procedure may create additional swelling and/or compression in the strain gauge cap 270. One or more of these or other factors (such as compression of the medical fluid or gas bubbles therein) may contribute to the overall capacitance volume of an injector system. Depending on the type of injection procedure or system, all of these factors may contribute to overall capacitance of the injector system or only a subset of these factors may contribute to overall capacitance of the injector system. The value of the contribution of each factor may differ from other factors.

While several different factors that can affect the overall flow rate or an individual flow rate of one of the fluids in the injector system have been described, it is also contemplated that other factors may also affect these flow rates. The state of the particular flow of fluid through the injector system and the particular flow transition physics (laminar versus turbulent flow) during fluid mixing, fluid flow past fluid path components, and exiting from the catheter into the patient's blood vessel, the temperature of the contrast medium may increase the viscosity of the contrast medium, and the higher flow rates for cardiac CT and other advanced imaging applications may also affect these flow rates.

A. Solutions for Reducing Spikes in Fluid Flow Rates and Providing Accurate Mixing Fluid Ratios Solutions to the problem of reducing backflow to compensate for system capacitance, for example in a high contrast medium-to-saline ratio, and thereby reducing undesired spikes in fluid flow rates and providing more accurate mixing ratios of fluids to the patient are described herein. In all of the examples described herein, a fluid flow profile of at least one of a first fluid 30 and a second fluid 32 is adjusted based on a function of the flow rate of one of the first fluid 30 and the second fluid 32 to minimize or dampen the spike or increase in the overall flow rate of fluid exiting from the catheter during a transition between delivering one of the first fluid 30 and the second fluid 32 to delivering the other of the first fluid 30 and the second fluid 32.

In one embodiment, one solution for improving (i.e., reducing) the overall capacitance of the injector system is to increase the stiffness of one or more of the components of the injector system subject to capacitance, to reduce swelling and/or compression in the one or more components. In one example, the stiffness of one of the catheter tubing 200, the catheter 210, the syringe 220, the syringe interface 230, the piston head 240, the piston 250, the polymeric cover 260, and the strain gauge cap 270 may be increased to reduce swelling and/or compression in the components of the injector system. In another embodiment, a pressure jacket may be placed around an outer surface of syringe 220 to reduce radial swelling under injection pressure.

The various embodiments of the methods described herein may be applied to injection procedures including simultaneous injection of fluid from two or more syringes or, alternatively, to reduce pressure and fluid flow spikes associated with transition from one fluid to another fluid during sequential injection of two or more fluids from two or more syringes, for example when transitioning from a contrast injection to a saline injection, or vice versa.

Figure 5:
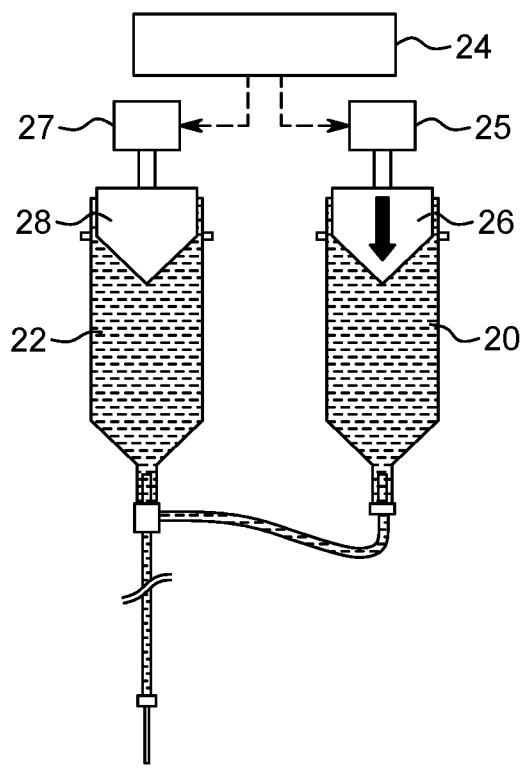
FIGS. 5 and 6 are schematic views depicting a fluid injection system according to one example of the present disclosure.
Figure 6:
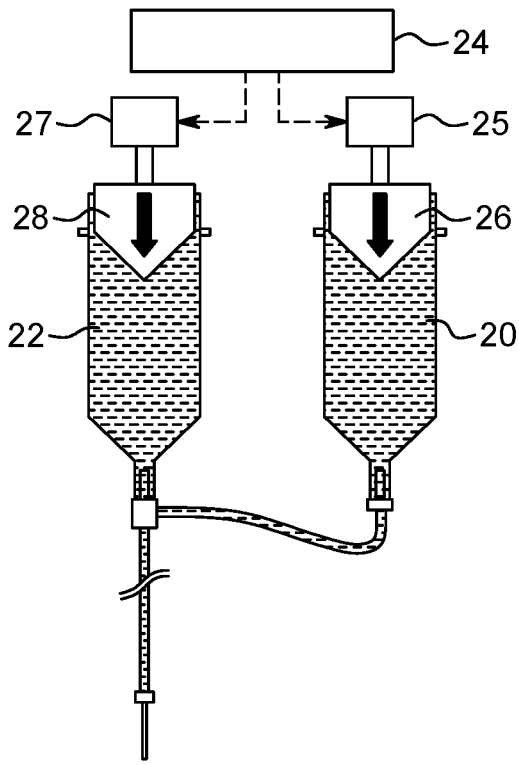

As shown in FIGS. 5 and 6, due to the additional time that is needed for the correct pressure to be achieved in the less viscous first fluid 20, various embodiments of the methods herein include delaying or ramping the application of pressure to the second fluid 22 until the pressure of the first fluid 20 has reached a predetermined pressure. This predetermined pressure may be a low equilibrium pressure that provides a smooth flow rate of fluid through the fluid injection system. In one example, the second fluid 22 may be more viscous than the first fluid 20. In one example, the second fluid 22 may be contrast medium and the first fluid 20 may be saline. As shown in FIG. 5, initially, pressure may be applied to the first fluid 20 via a plunger 26 until the pressure of the first fluid 20 has reached the predetermined pressure. As shown in FIG. 6, after the first fluid 20 has reached the predetermined pressure, the same predetermined pressure may be applied to the second fluid 22 via a plunger 28, resulting in the first fluid 20 and the second fluid 22 having a substantially similar flow rate through the fluid injection system. This system and method reduces the rapid increases in first fluid 20 pressure through the fluid injection system, which often causes erratic flow and inaccurate volumes of the first fluid 20 and the second fluid 22 being injected in the patient. By allowing the pressure of the first fluid 20 to reach a predetermined pressure before the second fluid 22, the first fluid 20 and the second fluid 22 can reach the same predetermined pressure at substantially the same time. The predetermined pressure will be dependent upon several factors, including, among others, the diameter of the catheter that is used to inject the first fluid 20 and the second fluid 22 into the patient, the viscosity of the first fluid 20 and the second fluid 22, the capacitance of the first fluid 20 and the second fluid 22 syringes and overall capacitance of the injector system, and/or the inner diameter of the tubing used to deliver the first fluid 20 and the second fluid 22 to the catheter. It is also contemplated that this fluid injection system may be automated with the use of a controller 24 that controls the actuation of each of a pair of motors 25, 27 that are configured to move the pair of plungers 26, 28 that are used to apply pressure to the first fluid 20 and the second fluid 22. In this example, the controller 24 may be programmed to delay applying or ramping the application of pressure to the second fluid 22 until the first fluid 20 has reached the predetermined pressure. The controller 24 may be a processor configured to store several different protocols for injection procedures based upon one or more of predetermined pressures for the fluid injection system, syringe volumes, catheter, the first fluid 20 type and/or volume to be delivered, the second fluid 22 type and/or volume to be delivered, flow rates of the first fluid 20 and/or the second fluid 22, system capacitance, fluid temperature, tubing type and/or diameter, and/or patient depending on the procedure. In one example, a user of the fluid injection system may input this identifying information into the controller 24, which will calculate the proper predetermined pressure to apply to the first fluid 20 and the second fluid 22 during the injection procedure to minimize pressure and flow spikes at fluid transitions. In an alternative example, the first fluid 20 may be more viscous than the second fluid 22. In this example, the process described above in reference to FIGS. 5 and 6, would be switched to apply an initial pressure to the second fluid 22 before applying pressure to the first fluid 20. It is also contemplated that the first fluid 20 and the second fluid 22 may have substantially equal viscosities. In this example, equal pressures may be applied to the first fluid 20 and the second fluid 22 at the outset of the process.

Figure 7:
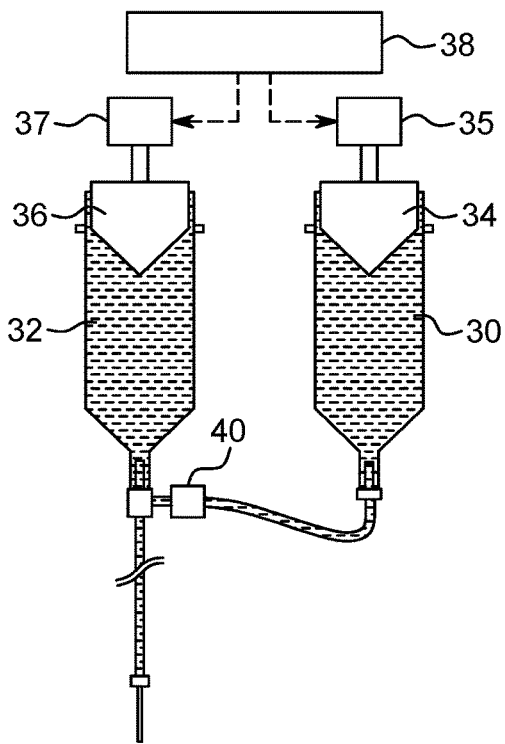
FIG. 7 is a schematic view depicting a fluid injection system according to another example of the present disclosure.

With reference to FIG. 7, another method for reducing undesired spikes in fluid flow rates and providing more accurate fluid mixing ratios with the fluid injection system is described. A first fluid 30 and a second fluid 32 may be provided in a fluid injection system in which plungers 34, 36 driven by motors 35, 37 apply pressure to the first fluid 30 and the second fluid 32, respectively. In one example, the second fluid 32 may be more viscous than the first fluid 30. The second fluid 32 may be contrast medium and the first fluid 30 may be saline. A controller 38 may be operatively connected to the motors 35, 37 to control the rate of pressure applied to the first fluid 30 and the second fluid 32 by the plungers 34, 36. The controller 38 may be programmed to apply pressure to the first fluid 30 based on the pressure that is being applied to the second fluid 32. As the second fluid 32 is pushed through the fluid injection system, the controller 38 may correspondingly change the pressure applied to the first fluid 30 by the plunger 34. For example, if a certain pressure is being applied to the second fluid 32 by the plunger 36, the controller 38 may instruct the plunger 34 to apply a proportionally larger pressure to the first fluid 30 to compensate for the resistance of the more viscous second fluid 32. Using the controller 38 in this manner, the first fluid 30 and the second fluid 32 may flow through the fluid injection system at substantially equal flow rates, thereby minimizing any erratic flow in the fluid injection system. In another example, the first fluid 30 may be more viscous than the second fluid 32. In this example, the process described above in reference to FIG. 7, would be switched to apply a proportionally larger pressure to the second fluid 32 in comparison to the pressure applied to the first fluid 30. It is also contemplated that the first fluid 30 and the second fluid 32 may have substantially equal viscosities. In this example, equal pressures may be applied to the first fluid 30 and the second fluid 32 at the outset. For example, in certain embodiments a more viscous fluid may be diluted with a less viscous fluid, or vice versa, so that the 4-Viscosity between the two injected fluids is minimized 4-Viscosity may also be reduced by heating a fluid having a higher viscosity, for example to a temperature close to body temperature, prior to the injection procedure.

Figure 37:
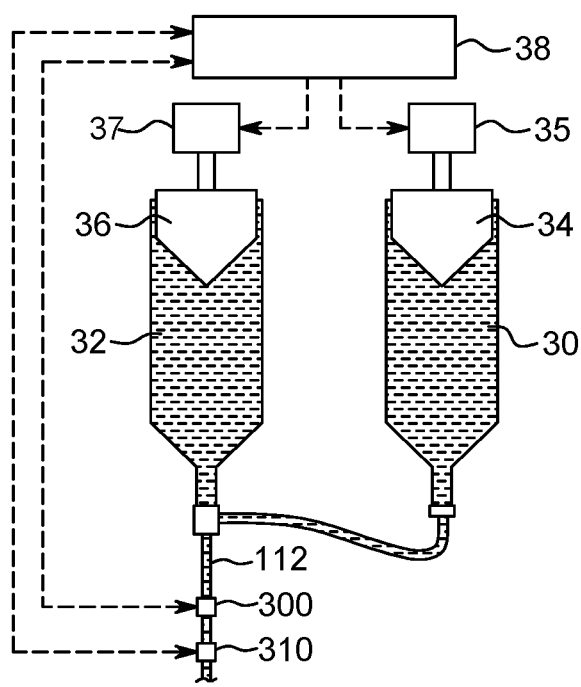
FIG. 37 is a schematic view depicting a fluid injection system according to another example of the present disclosure.

In another example, after pressure has been applied to the first fluid 30 and the second fluid 32, the flow rate of each fluid 30, 32 is measured. In the event the flow rates are not equal to one another, the fluid injection system may pause or hold the injection procedure, or pause injection or one or both fluids, to allow both fluids 30, 32 to achieve a steady-state pressure to reduce any stored energy in the fluid injection system. In one example, as the flow rates of the fluids 30, 32 are being measured, in the event it is determined that the flow rate of first fluid 30 is not equal to the flow rate of the second fluid 32 the fluid injection system can pause or hold the injection procedure while pressure is applied to either the first fluid 30 or the second fluid 32 to equalize the flow rates of the fluids 30, 32. In another example, the overall flow rate of the fluid exiting the catheter is measured during the injection procedure. The information regarding the overall flow rate is sent as real-time feedback information to the controller 38 to permit the controller 38 to adjust the pressures applied to the first fluid 30 and/or second fluid 32 to equalize the flow rates through the fluid injection system to ensure a consistent overall flow of fluid is exiting from the catheter into the patient's blood vessel. As shown in FIG. 37, in one example, a sensor 300, for example an ultrasonic mass flow rate sensor or other suitable flow rate sensor, is used to measure the overall flow rate in real-time of at least one of the first fluid 30 and second fluid 32 through the system. It is contemplated that the sensor 300 can be placed a various positions within the system. It is also contemplated that more than one sensor 300 is used to measure the overall flow rate of at least one of the first fluid 30 and the second fluid 32 at different positions in the system. In one example, the sensor 300 is a sensor that clips onto the exterior of the fluid path set 112 to the catheter. In another embodiment, the flow rate sensor may be internal and located within the fluid flow path. It is contemplated, however, that other flow rate sensing technologies could be used and alternative mounting scenarios could be used to position the sensor 300 on the fluid path set 112. The sensor 300 provides a real-time feedback loop to the controller 38 to control one or more of the injection parameters based on the overall flow rate measured by the sensor 300. In other embodiments, such a sensor arrangement could also be used with peristaltic systems and other continuous flow injector systems. In another example, an air sensor 310 is provided in line with the sensor 300 to measure the air content in the fluid flowing through the fluid path set 112. The information measured by the air sensor 310 may also be fed back to the controller 38 to control one or more of the injection parameters. For example, pressure applied to a plunger for a first viscous fluid 30 may be ramped down and pressure applied to a plunger of a second less viscous fluid 20 may be ramped up or one or more other fluid injection parameters may adjusted as appropriate so that the real-time feedback from a flow sensor indicates that the flow rate of the fluid exiting a catheter is substantially constant, for example not varying by more than 2.0 mL/sec, 1.5 mL/sec, 1.0 mL/sec, 0.5 mL/sec, 0.25 mL/sec, or even 0.1 mL/sec during transition from the first fluid 30 to the second fluid 20.

As further shown in FIG. 7, a check valve 40 may also be provided in the fluid injection system. The check valve 40 may be positioned in-line with the tubing of the first fluid 30. Using this check valve 40, the first fluid 30 will only flow into the second fluid 32 flow until a predetermined pressure is achieved by the first fluid 30. The predetermined pressure may be substantially equal to the desired flow rate pressure of the second fluid 32. The check valve 40 may be chosen based on the desired predetermined pressure. With the use of the check valve 40, the second fluid 32 is not permitted to flow back into the tubing of the first fluid 30, thereby reducing the expansion of the second fluid 32 syringe and/or first fluid 30 syringe under the extra pressure. In the example where the first fluid 30 is less viscous than the second fluid 32, the check valve 40 may be positioned in-line with the tubing of the first fluid 30 to prevent the first fluid 30 from opening the check valve 40 until a predetermined pressure has been applied to the first fluid 30. According to this example, capacitance build up in the first syringe 30 is reduced by eliminating any component from the pressure applied to the second fluid 32.

Figure 8:
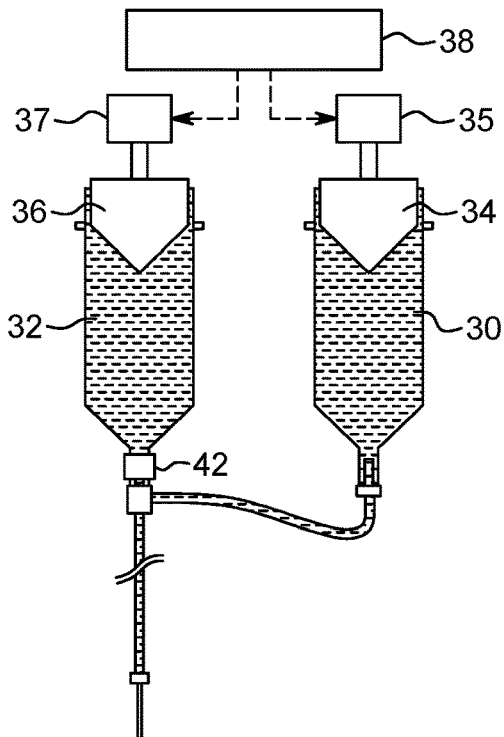
FIG. 8 is a schematic view depicting a fluid injection system according to another example of the present disclosure.

In a similar fashion, as shown in FIG. 8, a check valve 42 may be provided in-line with the tubing of the second fluid 32 portion of the fluid injection system. Similar to the check valve 40 on the first fluid 30 portion, the check valve 42 may be configured to control the flow of the second fluid 32 through the fluid injection system based on a desired predetermined pressure for the fluid injection system. The check valve 42 may be chosen according to the desired predetermined pressure. Using this system and method, the controller 38 may control the amount of pressure applied to the first fluid 30 and the second fluid 32 via the motors 35, 37 and plungers 34, 36. The controller 38 may monitor the pressures of the first fluid 30 and the second fluid 32 and adjust the plungers 34, 36 accordingly to maintain equal pressures in the fluid injection system. Using the check valve 42 on the second fluid 32 portion of the fluid injection system, the peak pressure values in the fluid injection system can be significantly lowered. Using this arrangement, the pressure of the first fluid 30 can reach a predetermined pressure, while the check valve 42 does not release the second fluid 32 until the predetermined pressure on the second fluid 32 is also achieved, thereby reducing the amount of second fluid 32 that backflows into the first fluid 30 portion of the fluid injection system. In one example, the first fluid 30 may be brought to the predetermined pressure and then the second fluid 32 may be subsequently pressurized to be released through the check valve 42. It is contemplated that the controller 38 can be programmed to initiate these pressurization procedures. In the example where the first fluid 30 is more viscous than the second fluid 32, the check valve 42 may be positioned in-line with the tubing of the second fluid 32 to prevent the second fluid 32 from opening the check valve 42 until a predetermined pressure has been applied to the second fluid 32.

Figure 9:
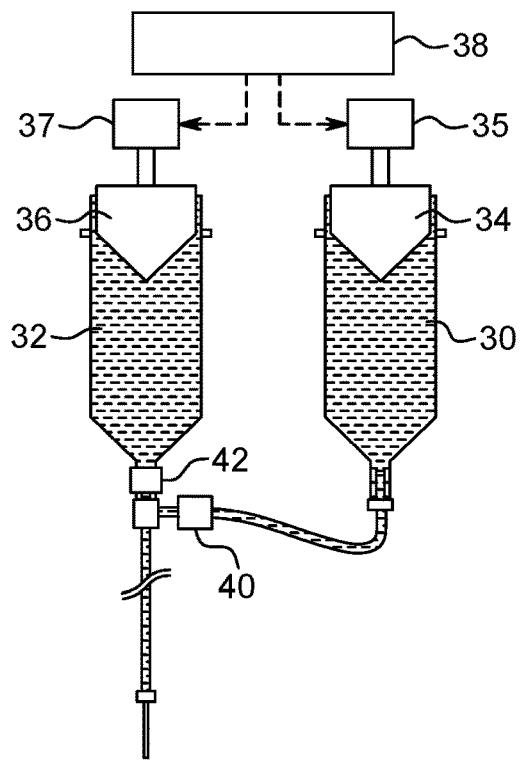
FIG. 9 is a schematic view depicting a fluid injection system according to another example of the present disclosure.

As shown in FIG. 9, it is also contemplated that the fluid injection system may include a check valve 40 on the first fluid 30 portion of the fluid injection system and a check valve 42 on the second fluid 32 portion of the fluid injection system. In this arrangement of the fluid injection system, fluid pressure from the non-active portion of the fluid injection system may be eliminated or isolated until the active portion of the fluid injection system reaches the same fluid pressure. For example, fluid pressure from the second fluid 32 may be eliminated or isolated in the fluid injection system until the fluid pressure of the first fluid 30 reaches a predetermined pressure or an equal pressure to the second fluid 32. The check valves 40, 42 may be chosen based on the desired predetermined pressure of the first fluid 30 and the second fluid 32. Using this arrangement, the first fluid 30 and the second fluid 32 are not mixed together in the fluid injection system until each fluid has reached the predetermined fluid pressure. A controller 38 may also be used in this arrangement to control the pair of motors 35, 37 that actuate the plungers 34, 36 that apply pressure to the first fluid 30 and the second fluid 32. The controller 38 may be preprogrammed with information regarding the threshold pressures for the check valves 40, 42, and user input on information on the first fluid 30 and second fluid 32 may be used to coordinate the proper pressures applied by the plungers 34, 36 to the first fluid 30 and the second fluid 32. In another example, the check valves 40, 42 may be high crack pressure check valves configured to reduce or essentially eliminate the backflow in the fluid injection system. The high crack pressure check valves 40, 42 may be check valves that allow flow in one direction with a relatively low pressure drop. The high crack pressure check valves 40, 42 may have a high opening or cracking pressure that may be above or near the maximum operating pressure of the fluid injection system. One example of such a high cracking pressure valve may include a spool valve having an internal sliding element that can block fluid flow. The valve may include a resistive force element, such as a spring or a pressurized bladder, to resist the movement of the sliding element. By providing the high crack pressure check valves 40, 42 with a high cracking pressure, no fluid may continue to flow or dribble out of the two syringes into the fluid path and possibly the patient until the requisite pressure balance is achieved in the fluid injection system. In another example, the open position of the check valves 40, 42 can be adjusted so that the check valves 40, 42 are partially open to control the flow of fluid through the check valves 40, 42. The check valves 40, 42 may be adjusted manually or automatically by the controller 38. Based on the flow rates of the first fluid 30 and/or the second fluid 32, the check valves 40, 42 can be partially opened, fully opened, or closed to achieve a desired flow rate of the fluid 30, 32 through the check valve 40, 42.

Figure 10:
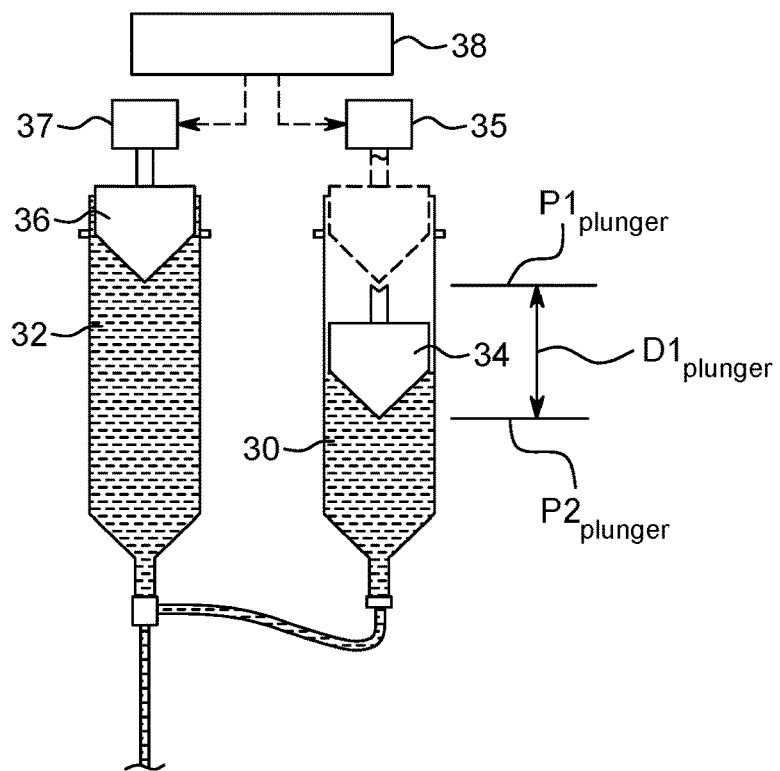
FIG. 10 is a schematic view depicting a fluid injection system according to another example of the present disclosure showing a plunger in an extended position.
Figure 11:
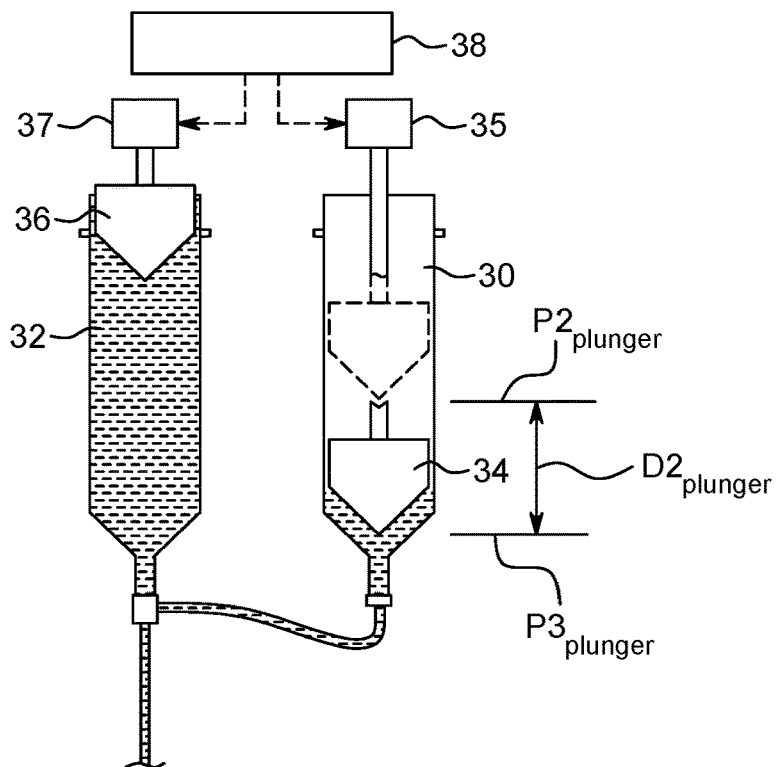
FIG. 11 is a schematic view depicting the fluid injection system of FIG. 10 with the plunger in an over-travel position.

As shown in FIGS. 10 and 11, another method of reducing undesired spikes in fluid flow rates in and providing accurate fluid mixing ratios to the patient is through the use of an over-travel and fast-controlled reverse pull of the plunger 34 within the first fluid 30 syringe to at least partially compensate for any undelivered first fluid 30 in the fluid injection system due to capacitance volume of the system. In this arrangement, the second fluid 32 may be more viscous than the first fluid 30. The over-travel position and fast-controlled reverse pull of the plunger 34 may be calculated according to the amount of potential stored volume in the first fluid 30 syringe based on the desired fluid pressure and the plunger 34 position at the end of the first fluid 30 injection procedure. To determine the length of over-travel for the plunger 34 needed to receive the desired volume of the first fluid 30, the following equation is used to calculate the plunger 34 over-travel distance, as identified in U.S. Patent Application Publication No. 2010/0222768 to Spohn et al., which is hereby incorporated by reference in its entirety:

$$\text{Over Travel (mL)} = C_1 + C_2 * x + C_3 * x^{\wedge 2} + C_4 * x^{\wedge 3} + C_5 * y + C_6 * y^{\wedge 2} + C_7 * y^{\wedge 3}$$

(Where: $C_1 = -0.811$; $C_2 = 0.039$; $C_3 = -0.00035$; $C_4 = 9.05\text{E-}7$; $C_5 = 0.0269$; $C_6 = -4.43\text{e-}5$; $C_7 = 2.607\text{e-}8$; x axis=pressure; y axis=position)

To receive the desired volume of the first fluid 30 from the fluid injection system, the plunger 34 must be over-traveled the same amount and then the plunger 34 is pulled back in reverse to compensate for release of the capacitance volume of the first fluid 30 syringe.

With reference to FIG. 10, upon activation of the controller 38, the motor 35 is activated to drive the plunger 34, which causes transition of the plunger 34 from a first initial position $P1_{plunger}$ (shown in dashed lines) to a second extended position $P2_{plunger}$, thereby advancing the plunger 34 a corresponding delivery distance $D1_{plunger}$. As the plunger 34 is transitioned across the delivery distance $D1_{plunger}$, a pre-set volume of the first fluid 30 is delivered from the interior of the first fluid 30 syringe to a downstream location. During delivery of the first fluid 30 from the interior of the syringe to the downstream location, the syringe swells and the system otherwise increases in capacitance volume as described herein, in such a manner that it is radially displaced from its initial configuration. As the plunger 34 is advanced longitudinally within the syringe to dispel liquid from the interior of the syringe, the first fluid 30 imparts an axial force to the wall of the syringe.

As shown in FIG. 11, in order to account for the under-delivery of fluid from the interior of the syringe due to the swelling of the syringe and other capacitance effects, the plunger 34 can be programmed to over-travel a sufficient longitudinal distance to compensate for system capacitance, such as the expansion of the syringe when under resulting axial pressure. In order to over-travel a specified longitudinal distance, the motor 35 is actuated by the controller 38, which causes further transition of the plunger 34 from the second extended position $P2_{plunger}$ (shown in dashed lines) to a third over-travel position $P3_{plunger}$, thereby advancing the plunger 34 a corresponding delivery distance $D2_{plunger}$. As the plunger 34 is transitioned across the delivery distance $D2_{plunger}$, a pre-determined volume of the first fluid 30 is delivered from the interior of the syringe to the downstream location to compensate for the under-delivery of fluid from the interior of the syringe as a result of the capacitance volume of the first fluid 30 syringe during transition from the first initial position to the second extended position.

Once forward longitudinal movement of the plunger 34 within the syringe is ceased, the plunger 34 may be rapidly driven back in order to compensate for the increased pressures within the fluid injection system resulting from the over-travel of the plunger 34. In order for the plunger 34 to retract to the retracted position, the controller 38 activates the motor 35, which causes transition of the plunger 34 from the third over-travel position $P3_{plunger}$ to the retracted position, thereby retracting the plunger 34 a corresponding retraction distance. This rapid backwards retraction of the plunger 34 relieves the swelling of the syringe and depressurizes the system. In one example, the rapid back-drive of the plunger 34 can be on the order of about 20 mL/s to 30 mL/s, for example 25 mL/s. This depressurization of the system allows the linear travel of the plunger 34 to coincide with the actual commanded location, irrespective of capacitance volume. In the example where the first fluid 30 is more viscous than the second fluid 32, the process described above in reference to FIGS. 10 and 11 would be switched to apply an over-travel and fast-controlled reverse pull of the plunger 36 within the second fluid 32 syringe to compensate for any undelivered second fluid 32 in the fluid injection system. It is also contemplated that the first fluid 30 and the second fluid 32 may have substantially equal viscosities. In this example, equal pressures may be applied to the first fluid 30 and the second fluid 32 at the outset of the process.

In typical fluid injection systems with saline and contrast medium fluids, the contrast medium has a higher viscosity than the saline. Due to this difference in viscosity, it is often difficult to apply the correct pressure to each fluid to achieve a uniform pressure between the two fluids to create a smooth flow of the mixture of the two fluids to the downstream location or sequential flow of the fluids without a flow spike at the fluid transition. As described herein, the higher viscosity of the contrast medium may cause backflow in the fluid injection system and/or swelling of the syringes holding the saline and/or contrast medium. Therefore, in one embodiment of the disclosure, the saline used in the fluid injection system may be replaced with an alternative fluid that has similar properties to saline but has a higher viscosity to substantially match the higher viscosity of the contrast medium. In one example, the saline may be replaced with a Ringers Lactate solution, which has a viscosity similar to blood or low viscosity contrast mediums. The pressure required to deliver the Ringers Lactate solution through the fluid injection system is higher than saline, which leads to a smaller difference between the pressure to move the Ringers Lactate solution and that needed to move the more viscous contrast medium resulting in lower spikes or jumps in the flow rates of the two fluids. The Ringers Lactate solution will also have a higher density than saline, which will reduce the density exchange between the Ringers Lactate solution and the contrast medium.

Figure 12:
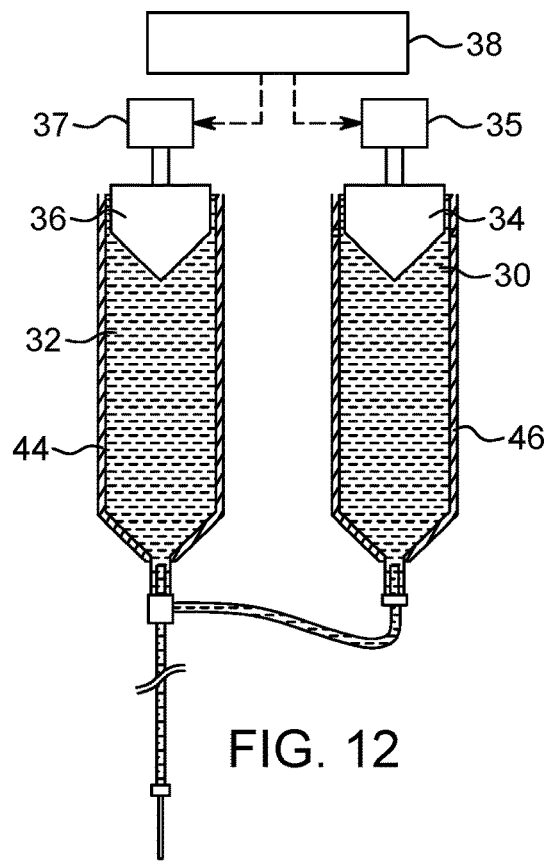
FIG. 12 is a schematic view depicting a fluid injection system according to another example of the present disclosure.

As shown in FIG. 12, in another example of the present disclosure, the second fluid 32 syringe may be designed with a lower capacitance (stored volume under pressure) than conventional syringes to reduce the effect of backflow into the second fluid 32 syringe. In one embodiment, the first fluid 30 may be more viscous than the second fluid 32. In an embodiment, a pressure jacket 44 may be provided around the outer surface of at least the second fluid 32 syringe to restrict the swelling in at least the second fluid 32 syringe due to backflow of second fluid 32. By providing the pressure jacket 44, the outer circumferential surface of the second fluid 32 syringe is reinforced, thereby limiting the amount of expansion or swelling in the second fluid 32 syringe. The pressure jacket 44 is configured to lower the capacitance of the second fluid 32 syringe, which results in a more accurate volume of the second fluid 32 being provided at the downstream location. The pressure jacket 44 may be made from a hard, medical-grade plastic, composite, or metal to provide the sufficient rigidity to the second fluid 32 syringe. It is also contemplated that an additional pressure jacket 46 may be provided around the outer circumferential surface of the first fluid 30 syringe. The pressure jacket 46 will assist in also lowering the capacitance of the first fluid 30 syringe, thereby providing more accurate volumes of the first fluid 30 at the downstream location. In the example where the second fluid 32 is more viscous than the first fluid 30, the pressure jacket 44 may be provided on the first fluid 30 syringe and the additional pressure jacket 46 may be provided on the second fluid 32 syringe.

Figure 13:
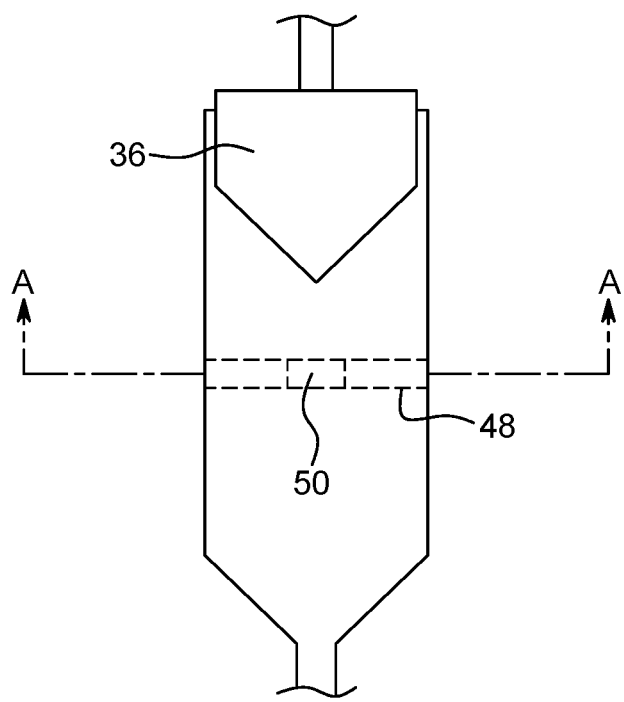
FIG. 13 is a front view of a syringe according to an example of the present disclosure.
Figure 14:
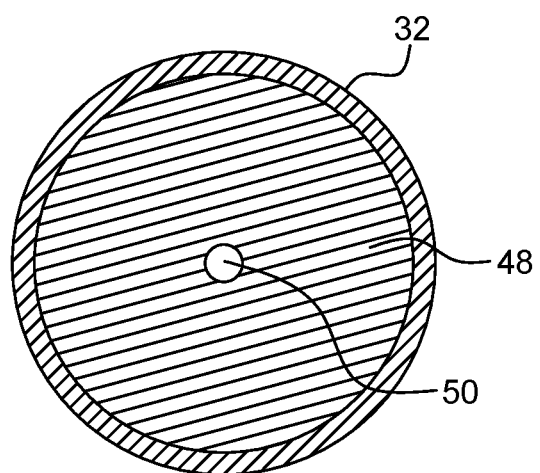
FIG. 14 is a cross-sectional view depicting a syringe of a fluid injection system according to another example of the present disclosure along line A-A in FIG. 13.
Figure 15:
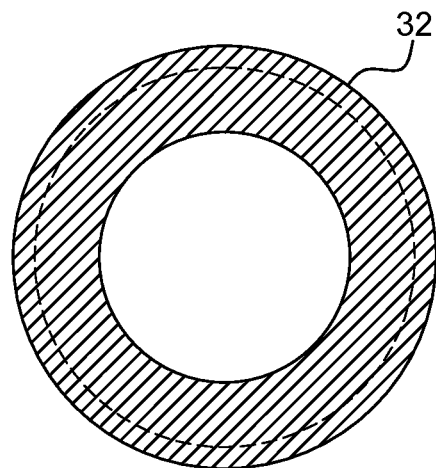
FIG. 15 is a cross-sectional view depicting a syringe of a fluid injection system according to another example of the present disclosure.

With reference to FIGS. 13-15, additional methods for reducing undesired spikes in fluid flow rates in the fluid injection system are described. In FIGS. 13 and 14, an obstruction member 48 may be provided in the second fluid 32 syringe to increase the fluid pressure of the second fluid 32 through the second fluid 32 syringe. In this example, the first fluid 30 may be more viscous than the second fluid 32. In one example, the obstruction member 48 may include an opening 50 configured to increase the fluid pressure of the second fluid 32 based on the desired fluid pressure through the fluid injection system. In one example, the opening 50 may be circular. However, it is contemplated that alternative shapes for the opening may be used, along with additional openings in the obstruction member 48. The obstruction member 48 is configured to increase the fluid pressure of the second fluid 32 so the second fluid 32 tubing of the fluid injection system does not decompress during the fluid injection process. Further, the increased fluid pressure of the second fluid 32 will decrease the amount of backflow that is directed to the second fluid 32 syringe, which may expand or swell the second fluid 32 syringe. The increased pressure of the second fluid 32 may be substantially equal to the pressure of the first fluid 30. In the example where the second fluid 32 is more viscous than the first fluid 30, the obstruction member 48 may be provided in the first fluid 30 syringe to increase the fluid pressure of the first fluid 30 through the first fluid 30 syringe.

Similar to the obstruction member 48 used in FIGS. 13 and 14 to obstruct the flow of the second fluid 32 through the second fluid 32 syringe, in another example of the disclosure the second fluid 32 syringe may include a reduced inner diameter to create a similar obstruction. As shown in FIG. 15, the inner diameter of the second fluid 32 syringe has been reduced from a larger diameter (shown in dashed lines) to a smaller diameter to increase the fluid pressure of the second fluid 32 through the fluid injection system. The inner diameter of the second fluid 32 syringe may be reduced in only a portion of the second fluid 32 syringe or the inner diameter of the second fluid 32 syringe may be reduced along the entire length of the second fluid 32 syringe. Similar to the obstruction member 48, the reduced inner diameter of the second fluid 32 syringe is configured to increase the fluid pressure of the second fluid 32 so the second fluid 32 tubing of the fluid injection system does not decompress during the fluid injection process. Further, the increased fluid pressure of the second fluid 32 will decrease the amount of backflow that is directed to the second fluid 32 syringe, which may result in the expansion or swelling of the second fluid 32 syringe. The reduced inner diameter will also assist in bringing the pressure of the second fluid 32 to a substantially equal pressure as the first fluid 30. In the example where the second fluid 32 is more viscous than the first fluid 30, the inner diameter of the first fluid 30 syringe may be reduced to create a similar obstruction.

Figure 16:
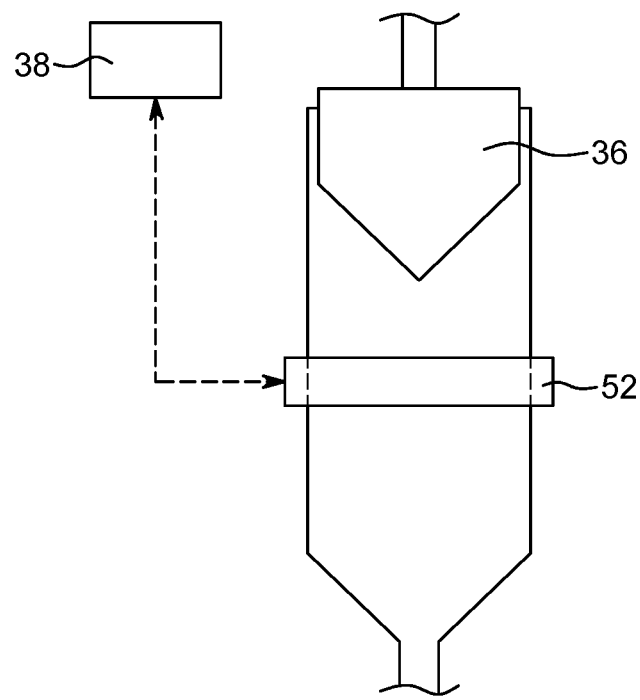
FIG. 16 is a schematic view depicting a fluid injection system according to another example of the present disclosure.

With reference to FIG. 16, another method of reducing undesired spikes in fluid flow rates is described. In this example, the first fluid 30 may be more viscous than the second fluid 32. In this example, an external restriction member 52 may be provided around at least a portion of the outer circumferential surface of the second fluid 32 syringe. The external restriction member 52 may be cylindrical in shape. However, it is contemplated that alternative shapes and sizes may be used with the second fluid 32 syringe. The external restriction member 52 may define an aperture through which the second fluid 32 syringe may be inserted. The external restriction member 52 may be provided via a friction-fit on the second fluid 32 syringe to control the flow rate of the second fluid 32 through the second fluid 32 syringe. The external restriction member 52 may reduce the swelling or expansion of the second fluid 32 syringe due to any backflow into the second fluid 32 syringe, thereby reducing the capacitance of the second fluid 32 syringe. The external restriction member 52 may apply pressure to the outer surface of the second fluid 32 syringe, thereby restricting the flow of the second fluid 32 through the second fluid 32 syringe. Pressure may be applied by the external restriction member 52 by decreasing the diameter of the aperture defined by the external restriction member 52. It is also contemplated that the pressure applied by the external restriction member 52 may be controlled by the controller 38. The controller 38 may be programmed to adjust the pressure applied by the external restriction member 52 and the diameter size of the aperture defined by the external restriction member 52 based on the fluid pressures in the fluid injection system, the capacitance of the second fluid 32 syringe and the first fluid 30 syringe, the catheter size, and the viscosities of the second fluid 32 and the first fluid 30, among other factors. The controller 38 may also be programmed to adjust the diameter size of the aperture defined by the external restriction member 52 based on the timing of the fluid injection procedure. In the example where the second fluid 32 is more viscous than the first fluid 30, the external restriction member 52 may be provided around a portion of the outer circumferential surface of the first fluid 30 syringe.

Figure 17:
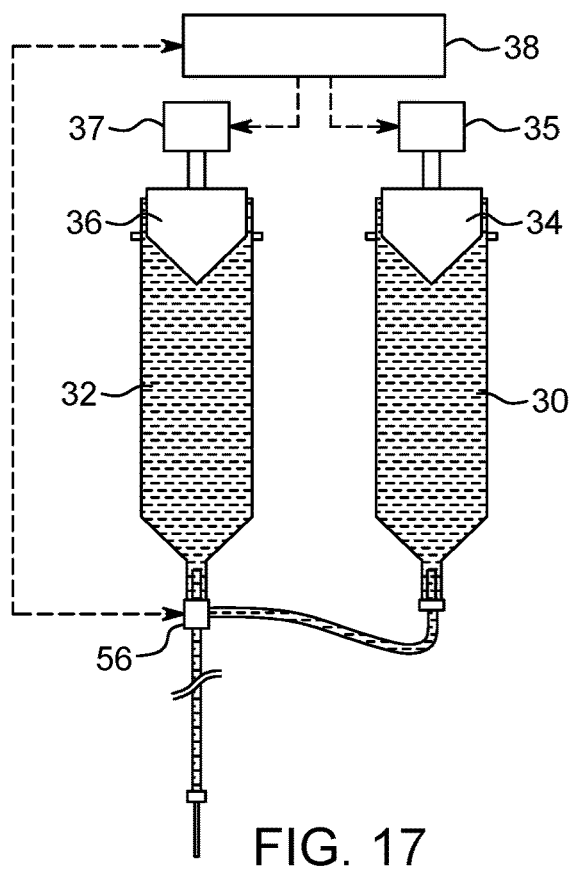
FIG. 17 is a schematic view depicting a fluid injection system according to another example of the present disclosure.

With reference to FIG. 17, another method of reducing undesired spikes in fluid flow rates is described. In this example, the second fluid 32 may be more viscous than the first fluid 30. This method includes the use of an equalizing flow valve 56 to monitor and control the flow rates of the first fluid 30 and the second fluid 32. The equalizing flow valve 56 may be positioned in the fluid injection system at a location where the first fluid 30 tubing and the second fluid 32 tubing connect with one another. The equalizing flow valve 56 may monitor the flow rates of the first fluid 30 and the second fluid 32 and adjust an orifice defined by the equalizing flow valve 56 to maintain the desired delivery flow rates of the two fluids. In one example, the equalizing flow valve 56 may be connected to a controller 38, which also actuates the motors 35, 37 that drive the plungers 34, 36 in the fluid injection system based on real-time feedback readings from equalizing flow valve 56. Using the controller 38 with the equalizing flow valve 56, the pressure applied by the plungers 34, 36 can be adjusted according to the flow rates of the two fluids through the equalizing flow valve 56. The controller 38 may be programmed to read the flow rates of the two fluids through the equalizing flow valve 56 and adjust the pressure applied by the plungers 34, 36 accordingly to ensure that the second fluid 32 and the first fluid 30 have substantially equal pressures. Alternatively, the controller 38 and/or equalizing flow valve 56 may be pre-programmed according to the types of fluids used in the fluid injection system, fluid volumes, syringe features, catheter size, the capacitance of the fluid injection system, and/or the desired flow rates of the two fluids, which information may be stored in the controller 38. An operator may manually input the information regarding the fluid injection system into the controller 38, which will assist in adjusting the plunger 34, 36 pressure and/or the equalizing flow valve 56 accordingly to obtain the desired flow rates of the two fluids.

Figure 18:
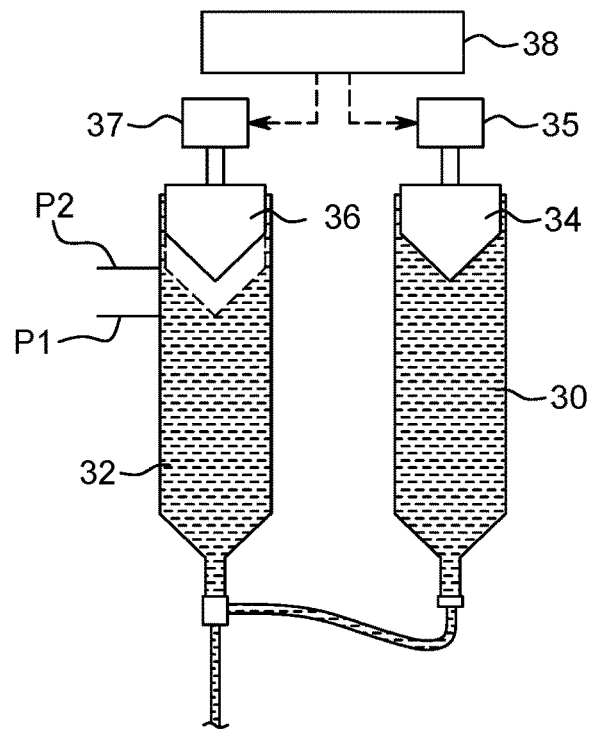
FIG. 18 is a schematic view depicting a fluid injection system according to another example of the present disclosure.

With reference to FIG. 18, another method of reducing undesired spikes in fluid flow rates is described. In this example, the first fluid 30 may be more viscous than the second fluid 32. According to this embodiment, during operation of the fluid injection system, an operator will likely know the pressures that are to be applied by the plungers 34, 36 and the volume of the first fluid 30 and the second fluid 32 in the fluid injection system. By determining the capacitance of the second fluid 32 syringe, the operator can adjust the plunger 36 of the second fluid 32 syringe accordingly to account for the extra stored volume of the second fluid 32 due to the capacitance of the second fluid 32 syringe. Using this method, the plunger 36 may be pulled back from the second fluid 32 syringe equal to a capacitance volume of the second fluid 32 syringe, which will reduce the pressure to zero in the second fluid 32 syringe. The second fluid 32 may then be injected at the desired flow rate without experiencing any swelling or expansion in the second fluid 32 syringe. It is also contemplated that the plunger 36 may be pulled back by an instruction from the controller 38. Based on information regarding the fluid injection system, such as, fluid viscosities, catheter size, capacitance of the second fluid 32 syringe, and/or the volume of fluid in the fluid injection system, the controller 38 may be programmed to pull the plunger 36 from the second fluid 32 syringe in an amount equal to the capacitance volume of the second fluid 32 syringe. For example, if the second fluid 32 syringe capacitance is 10 mL, the plunger 32 may be pulled from a starting position P1 (shown in dashed lines) to a new position P2 to compensate for the extra volume that will be stored in the second fluid 32 syringe during the fluid injection procedure. In the example where the second fluid 32 is more viscous than the first fluid 30, the process described above with reference to FIG. 18 may be used with the first fluid 30 syringe.

According to an embodiment, in a similar method, a test injection procedure using the first fluid 30 and second fluid 32 may be performed before the actual diagnostic phase, using the same flow rates as will be used from the diagnostic injection procedure. A pressure measurement of the first fluid 30 phase is obtained during the test injection procedure, which gives an indication of the expected pressure for the programmed flow rate under the current tubing and patient conditions. This measured pressure value is recorded and used during the diagnostic injection procedure to modify the flow rate of at least one of the first fluid 30 and the second fluid 32 to modify the flow rate and fluid flow profile of at least one of the first fluid 30 and the second fluid 32 to compensate for capacitance in the injector system. In one example, the flow rate modification is achieved by temporarily changing a pressure limit of one of the fluids 30, 32 in an adaptive flow algorithm used by a controller 38 to control the pressures of the fluid injection system. In another embodiment, a series of flow algorithms may be programmed into a controller 38 or processor based on set of pre-programmed injection protocols. Alternatively, one or more algorithms may be determined and programmed into the controller 38 that utilize various system parameters for a specific injection setup and protocol, such as, for example, fluid volumes and types, temperature, syringe volumes and types, desired flow rates, target organ or body part for imaging, patient information, etc., where the algorithms utilize the various parameters to calculate and appropriate injection protocol for the injection procedure.

Figure 28:
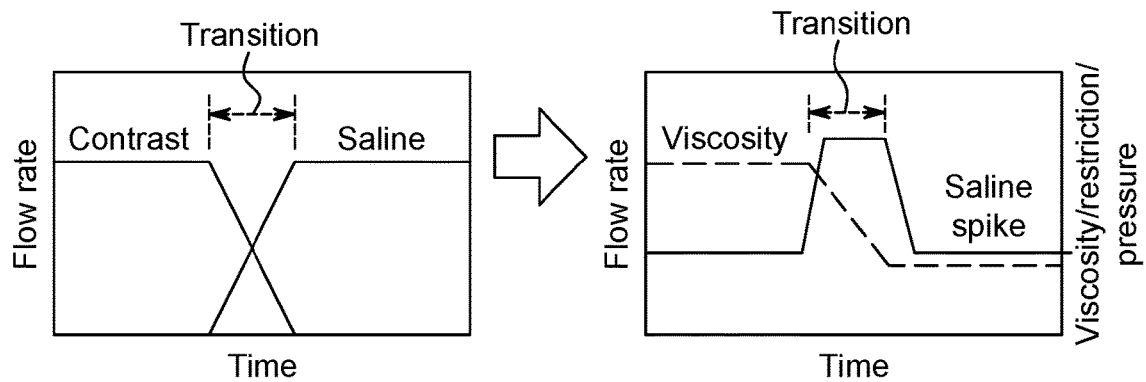
FIG. 28 is a graphical illustration of a transition period between injecting contrast medium and injecting saline during current multi-fluid injection procedures.
Figure 29:
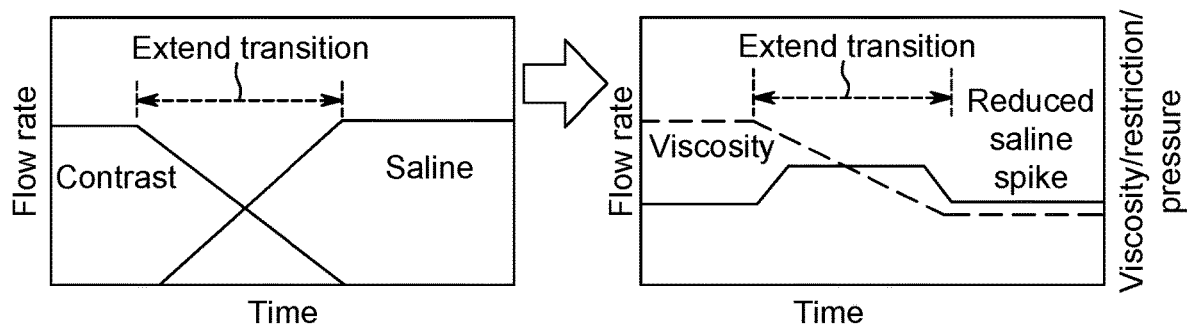
FIG. 29 is a graphical illustration of an extended transition period between injecting contrast medium and injecting saline according to the present disclosure.

With reference to FIGS. 28 and 29, another embodiment of a method of providing more accurate mixing ratios is described. During current multi-fluid injection procedures, a spike in saline flow rate may occur when the fluid passing through the catheter suddenly changes in viscosity, for example during a transition from contrast to saline, resulting in a drop in the pressure at the restriction point of the catheter. During this period of pressure drop, any fluid stored in the compliance of a disposable set or system capacitance holding the fluid is released through the catheter. As shown in FIG. 28, contrast medium is initially directed through the catheter. After the contrast medium has been injected, the saline is injected and begins to flow through the catheter. A transition period occurs when the flow rate of the contrast medium begins to decrease through the catheter and the flow rate of the saline begins to increase through the catheter. During this transition period, the viscosity of the fluid flowing through the catheter suddenly and quickly changes, which results in a spike of the saline flow rate through the catheter. Due to the short transition period that occurs during the switch between injecting the contrast medium and injecting the saline, an increased drop in pressure is created, which causes an increased saline flow rate spike in the fluid exiting the catheter.

As shown in one embodiment in FIG. 29, by extending the transition period between injecting the contrast medium and injecting the saline, a more gradual viscosity/pressure gradient may be achieved during the injection procedure. With this extended transition period, the same volume of fluid is released over a longer period of time, so the average flow rate magnitude of the saline spike is reduced. The flow rate of the contrast medium is gradually and slowly reduced, while the flow rate of saline is gradually and slowly increased. The change in viscosity of the fluid through the catheter is gradual, resulting in a decreased drop of the pressure in the catheter. The extended transition period may be achieved in such a manner that does not increase the volume of contrast medium that is delivered during the injection procedure and does not degrade the efficacy of the injection procedure. It is also contemplated that non-linear or non-continuous extended transition periods could be used, which would result in less impact to the image taken of the patient, and taking advantage of the fluid dynamics of the fluid injection system. In other embodiments, real-time fluid flow rate measurements in a feedback loop to a processor may allow the processor to adjust the contrast and saline flow rates appropriately to minimize any spike in fluid flow rate during transition from one fluid to another.

In another example, the viscosity of the first fluid 30 or the second fluid 32 is adjusted to minimize or dampen the spike or increase in the overall flow rate during a transition between delivering one of the first fluid 30 and the second fluid 32 to delivering the other of the first fluid 30 and the second fluid 32. In one example, a volume of the first fluid 30 is added to the second fluid 32 to dilute the overall viscosity of the second fluid 32. Since the first fluid 30 has a lower viscosity, the first fluid 30 will dilute the second fluid 32 and reduce the overall viscosity of the second fluid 32. In another example, the viscosity of the first fluid 32 is increased to match the viscosity of the second fluid 32. By equalizing the viscosities of the fluids 30, 32, the transition of flow between the delivery of one of the first fluid 30 and the second fluid 32 and the delivery of the other of the first fluid 30 and the second fluid 32 does not create such a large spike or increase in the overall flow rate exiting from the catheter.

B. Solutions for Reducing Catheter Kickback and Rapid Movement

With reference to FIGS. 19-27, several methods are described for reducing undesired spikes in fluid flow rates by using several different catheter designs to control the erratic flow of fluid to the patient's blood vessel. The following methods are configured to reduce the amount of kick-back or pull out the catheter experiences when the erratic flow of the contrast medium is delivered through the fluid injection system.

Figure 19:
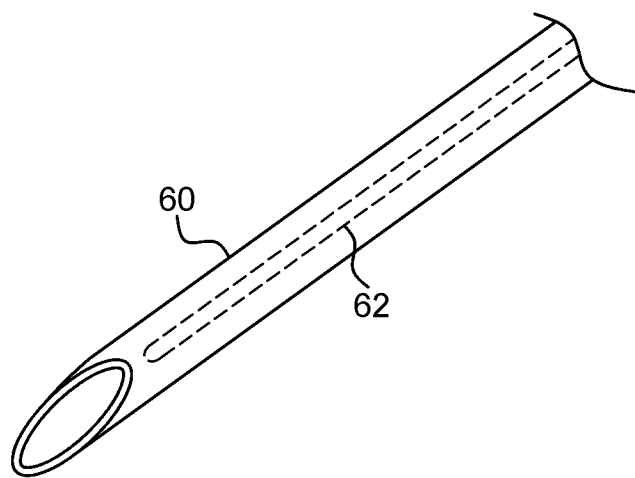
FIG. 19 is a front view of a catheter including a rigid member according to another example of the present disclosure.

As shown in FIG. 19, one method of reducing kick-back in the catheter 60 is to provide a rigid member 62 along the longitudinal length of the catheter 60. In one example, the rigid member 62 may be a wire. The rigid member 62 may be attached to the outer surface of the catheter 60 or embedded in the walls of the catheter 60. The rigid member 62 may be configured to stiffen the catheter 60 from bending during injection of the erratic fluid from the fluid injection system. By stiffening the catheter 60 with the rigid member 62, the catheter 60 may be less likely to kick-back or pull out of the injection site when the erratic flow is delivered through the catheter 60. By reducing the kick-back of the catheter 60, the catheter 60 may be less likely to extend into the surrounding tissue of the patient.

Figure 20A:
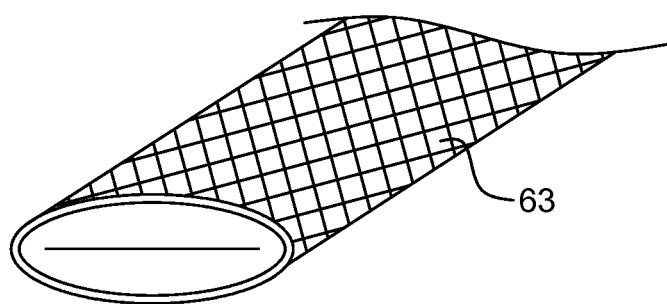
FIG. 20A is a front view of a catheter including a sheath provided on an outer circumferential surface thereof in a deflated position.
Figure 20B:
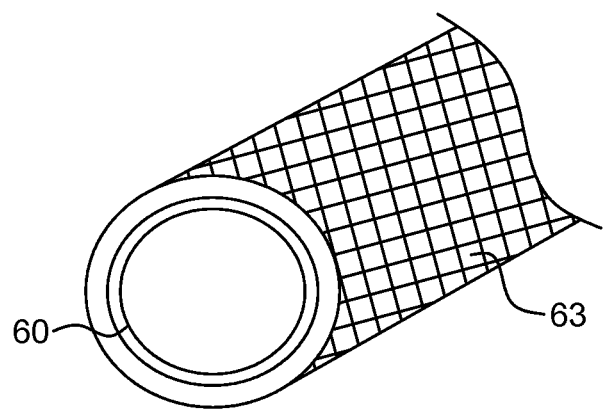
FIG. 20B is a front view of the catheter and sheath of FIG. 20A in an inflated position.

As shown in FIGS. 20A and 20B, another method of reducing kick-back in the catheter 60 is to provide a sheath or braided member 63 on an outer circumferential surface of the catheter 60. The sheath 63 may extend along the length of the catheter 60 or may only be provided on a distal end of the catheter 60. In one example, the inner diameter of the sheath 63 may be substantially equal to the outer diameter of the catheter 60 so that the catheter 60 may fit within the sheath 63. The sheath 63 may be made of stainless steel wire interlaced together, nylon, Kevlar, spectra fiber, or any other suitably flexible material that is safe to insert into a patient's blood vessel. Initially, before injection of fluid through the catheter 60, the sheath 63 and catheter 60 are substantially deflated within the patient's blood vessel (FIG. 20A). As fluid is injected through the catheter 60, the fluid expands the inner diameter of the catheter 60 to permit fluid to flow therethrough (FIG. 20B). As the catheter 60 expands against the inner diameter of the sheath 63, the sheath 63 also begins to expand. The catheter 60 expands until the catheter 60 and the sheath 63 have expanded to their respective maximum outer diameters. The outer diameter of the sheath 63 may be substantially equal to an inner diameter of at least a portion of a blood vessel so that the outer diameter of the catheter 60 is constrained by the sheath 63 to keep the catheter 60 from expanding to a diameter larger than the diameter of a blood vessel. By keeping the outer diameter of the catheter 60 smaller than the blood vessel, the fluid exiting the catheter 60 remains coaxial with the catheter 60. Since the inner diameter of the catheter 60 expands slowly under pressure when initially deflated, the jetting velocity and acceleration of the fluid through the catheter 60 is reduced, which also reduces any kick-back or rapid movement of the catheter 60 in the patient's blood vessel. Further, as sheath 63 expands against the inner wall of at least a portion of the patient's blood vessel, the sheath 63 may be secured to the inner walls to stabilize catheter 60 within the blood vessel or may seal the needle hole entrance in the blood vessel, thereby reducing the risk of rapid movement of the catheter.

Figure 21:
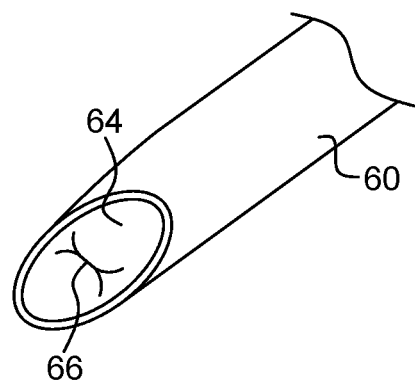
FIGS. 21 and 22 are front views of a catheter according to another example of the present disclosure.
Figure 22:
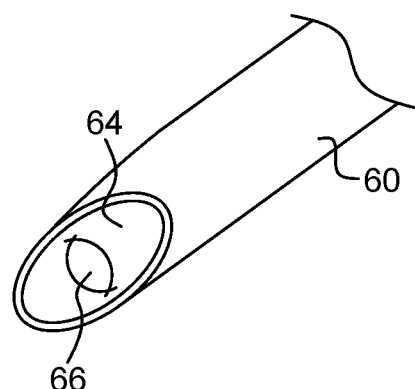

As shown in FIGS. 21 and 22, another method of reducing kick-back in the catheter 60 is to provide a split tip 64 on the distal end of the catheter 60. The split tip 64 may define an aperture 66 through which the fluid may be delivered to the patient. As shown in FIG. 21, the split tip 64 may be configured to remain in a closed position in which the aperture 66 also remains closed. In this example, the split tip 64 will not open until a predetermined or sufficient pressure is provided by the fluid in the catheter 60. With reference to FIG. 22, upon reaching this predetermined pressure, the aperture 66 of the split tip 64 will open and allow the fluid to be delivered into the patient's vein. The split tip 64 assists in reducing the erratic flow of the fluid that is permitted to exit from the catheter 60. The fluid is unable to exit into the patient's vein until the predetermined pressure is achieved, which stabilizes the fluid in the catheter 60 before injection into the patient. It is also contemplated that different shapes and number of apertures in the split tip 64 may be utilized to improve the stability of the catheter 60.

Figure 23:
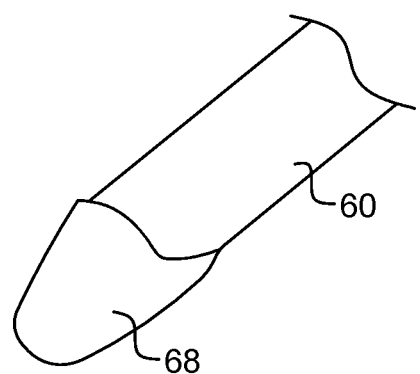
FIGS. 23 and 24 are front views of a catheter according to another example of the present disclosure.
Figure 24:
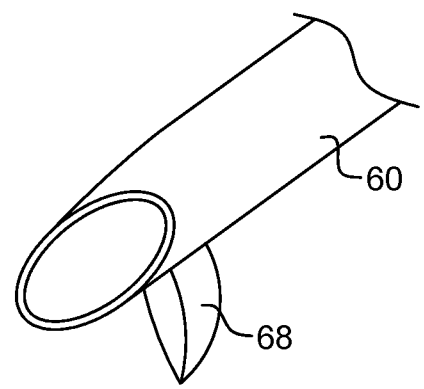

As shown in FIGS. 23 and 24, similar to the split tip 64 of FIGS. 21 and 22, another method of reducing kick-back in the catheter 60 includes providing an over-molded tip 68 on the distal end of the catheter 60. The over-molded tip 68 may be configured to overlap the distal end of the catheter 60. The over-molded tip 68 may be configured to open and allow the fluid to exit the distal end of the catheter 60 upon the fluid reaching a predetermined or threshold pressure. As shown in FIG. 23, the over-molded tip 68 is configured to remain closed during use of the catheter 60, until a certain pressure is obtained by the fluid. Once the fluid pressure has increased to the threshold pressure, the over-molded tip 68 will open and move away from the opening of the distal end of the catheter 60 (as shown in FIG. 24), thereby permitting the fluid to exit into the patient's blood vessel. The over-molded tip 68 assists in reducing the erratic flow of the fluid that is permitted to exit from the catheter 60. The fluid is unable to exit into the patient's vein until the predetermined pressure is achieved, which stabilizes the fluid in the catheter 60 before injection into the patient. It is also contemplated that different shapes of the over-molded tip 68 may be utilized to improve the stability of the catheter 60.

Figure 25:
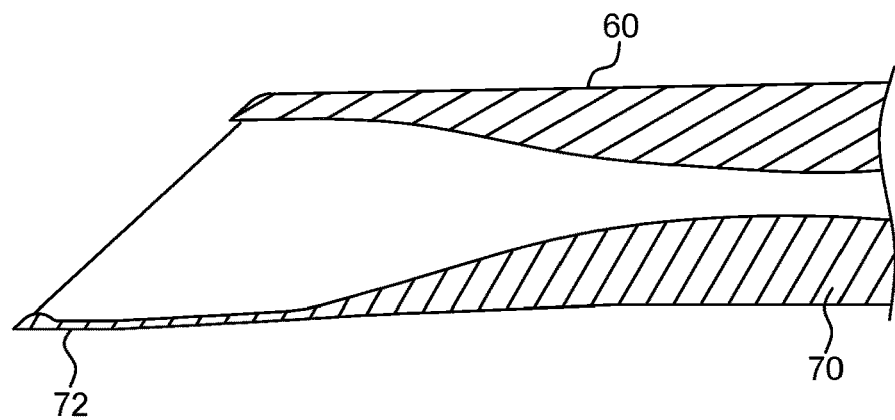
FIG. 25 is a cross-sectional view of a catheter according to another example of the present disclosure.

With reference to FIG. 25, another method of reducing kick-back in the catheter 60 includes tapering the inside diameter of the catheter 60 to allow more steady flow of fluid through the catheter 60. In one example, the inner diameter may start at a smaller dimension at a proximal end 70 of the catheter 60. In this example, the inner diameter will taper or increase outwardly to the distal end 72 of the catheter 60, which will have a larger inner diameter than the proximal end 70. By tapering the inner diameter in this fashion such that the proximal end has a smaller diameter, a reduction in the proximal hoop stress on the catheter 60 tubing at the proximal end 70 of the catheter 60 is achieved, and a reduction in the kick-back or rapid movement of the catheter 60 by lowering the acceleration of the fluid as it exits the catheter 60 may be achieved. It is contemplated that the catheter 60 may begin to taper at different locations along the length of the catheter 60. However, proximal end 70 of the catheter 60 will always have a smaller inner diameter than the distal end 72 of catheter 60. It is contemplated that the dimensions of the inner diameter at proximal end 70 and distal end 72 may vary in catheter 60.

Figure 26:
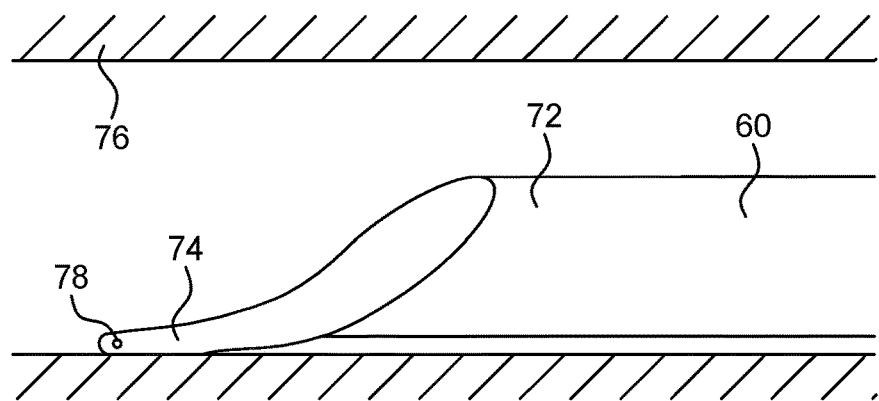
FIGS. 26 and 27 are cross-sectional views of a catheter inserted into a patient's blood vessel according to another example of the present disclosure.
Figure 27:
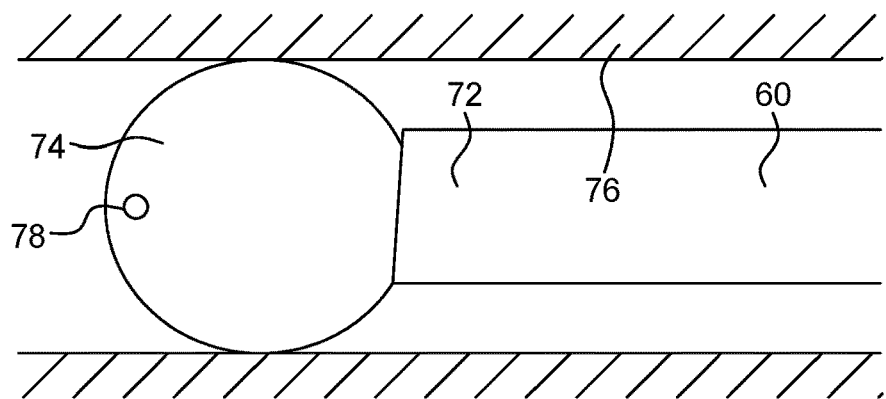

With reference to FIGS. 26 and 27, another method of reducing kick-back in the catheter 60 includes providing a balloon tip 74 on an end of the catheter 60. The balloon tip 74 may be made from a flexible material so the balloon tip 74 can be stretched. The balloon tip 74 may be inflatable and deflatable based on the amount of fluid that is directed through the balloon tip 74. The balloon tip 74 may be provided on the distal end 72 of the catheter 60. As shown in FIG. 26, when fluid is not being provided through the catheter 60, the balloon tip 74 is deflated and rests in the blood vessel 76 of the patient on the distal end 72 of the catheter 60. As shown in FIG. 27, upon fluid being injected through the catheter 60, the balloon tip 74 is inflated by the liquid and is directed out of the balloon tip 74 via an aperture 78. When fluid is directed through the balloon tip 74, the balloon tip 74 is expanded to substantially the same inner diameter size as the blood vessel 76. The balloon tip 74 may assist in centering the flow of the liquid through the blood vessel 76. The balloon tip 74 may also anchor the catheter 60 to the inner walls of the blood vessel 76 to seal any puncture holes in the blood vessel 76 from leaking any injected fluid into the surrounding tissue. This sealing feature is particularly advantageous when the catheter 60 punctures through both walls of the blood vessel 76 and is then slightly pulled back into the blood vessel 76. The balloon tip 74 will assist in sealing any accidental punctures in the blood vessel 76 walls to reduce any contrast medium or saline leaking into the surrounding tissue.

While several examples of a fluid injection system and catheter are shown in the accompanying figures and described hereinabove in detail, other examples will be apparent to, and readily made by, those skilled in the art without departing from the scope and spirit of the disclosure. For example, it is to be understood that this disclosure contemplates that, to the extent possible, one or more features of any example can be combined with one or more features of any other example. Accordingly, the foregoing description is intended to be illustrative rather than restrictive.

What is claimed is:

1. A method of maintaining an overall flow rate during a sequential delivery of at least two fluids to a patient's blood vessel, the method comprising:
    delivering at least a first fluid into the patient's blood vessel at a first flow rate;
    delivering at least a second fluid into the patient's blood vessel at a second flow rate; and
    adjusting at least one of a first flow profile of the first flow rate and a second flow profile of the second flow rate to dampen a transient increase in the overall flow rate during a transition between delivering one of the first fluid and the second fluid to delivering the other of the first fluid and the second fluid.

2. The method of claim 1, wherein adjusting at least one of the first flow profile of the first flow rate and a second flow profile of the second flow rate comprises delaying a delivery of one of the first fluid and the second fluid until the other of the first fluid and the second fluid reaches a predetermined flow rate.

3. The method of claim 1, wherein adjusting at least one of the first flow profile of the first flow rate and a second flow profile of the second flow rate comprises adjusting one of the first flow rate and the second flow rate using a controller, wherein the adjusting is based on the other of the first flow rate and the second flow rate.

4. The method of claim 1, further comprising pressurizing the first fluid using a first check valve to a first predetermined pressure before delivering the first fluid.

5. The method of claim 1, further comprising pressurizing the second fluid using a second check valve to a second predetermined pressure before delivering the second fluid.

6. The method of claim 1, further comprising pressurizing the first fluid and the second fluid using a first check valve and a second check valve to a first predetermined pressure and a second predetermined pressure, respectively, before delivering the first fluid and the second fluid.

7. The method of claim 1, wherein adjusting at least one of the first flow profile of the first flow rate and a second flow profile of the second flow rate comprises over-delivering a predetermined volume of at least one of the first fluid and the second fluid during the delivery of the at least one of the first fluid and the second fluid.

8. The method of claim 1, further comprising diluting one of the first fluid and the second fluid with a predetermined volume of the other of the first fluid and the second fluid.

9. The method of claim 1, further comprising:
    providing a multi-fluid injection system comprising:
        a first syringe for receiving the first fluid and a first plunger movable within a barrel of the first syringe to pressurize the first fluid for delivery to the patient's blood vessel; and
        a second syringe for receiving the second fluid and a second plunger movable within a barrel of the second syringe to pressurize the second fluid for delivery to the patient's blood vessel; and
    reducing a capacitance of at least one of the first syringe and the second syringe to prevent backflow of at least one of the second fluid into the first syringe and the first fluid into the second syringe.

10. The method of claim 9, further comprising providing a pressure jacket around an outer circumference of at least one of the first syringe and the second syringe to reduce the capacitance of the at least one of the first syringe and the second syringe when the at least one of the first syringe and the second syringe is under pressure.

11. The method of claim 1, further comprising:
    providing a multi-fluid injection system comprising:
        a first syringe for receiving the first fluid and a first plunger movable within a barrel of the first syringe to pressurize the first fluid for delivery to the patient's blood vessel; and
        a second syringe for receiving the second fluid and a second plunger movable within a barrel of the second syringe to pressurize the second fluid for delivery to the patient's blood vessel,
    wherein at least one of the first syringe and the second syringe includes a reduced inner diameter to correspond to a desired flow rate.

12. The method of claim 11, further comprising providing an obstruction member within at least one of the first syringe and the second syringe to reduce the inner diameter of at least one of the first syringe and the second syringe.

13. The method of claim 1, further comprising:
    providing a multi-fluid injection system comprising:
        a first syringe for receiving the first fluid and a first plunger movable within a barrel of the first syringe to pressurize the first fluid for delivery to the patient's blood vessel; and
        a second syringe for receiving the second fluid and a second plunger movable within a barrel of the second syringe to pressurize the second fluid for delivery to the patient's blood vessel;
    providing an external restriction member on an outer circumference of at least one of the first syringe and the second syringe; and
    adjusting an inner diameter of the external restriction member to adjust a permitted swelling of the at least one of the first syringe and the second syringe.

14. The method of claim 1, wherein adjusting at least one of the first flow profile of the first flow rate and a second flow profile of the second flow rate comprises controlling one of the first flow rate and the second flow rate using an equalizing flow valve based on the other of the first flow rate and the second flow rate.

15. The method of claim 1, wherein adjusting at least one of the first flow profile of the first flow rate and a second flow profile of the second flow rate comprises adjusting at least one of the first flow rate and the second flow rate before delivery of at least one of the first fluid and the second fluid based on at least one of known operating fluid pressure and capacitance of a multi-fluid injection system used to deliver the first fluid and the second fluid.

16. The method of claim 1, wherein adjusting at least one of the first flow profile of the first flow rate and a second flow profile of the second flow rate comprises increasing a transition time between delivering one of the first fluid and the second fluid and delivering the other of first fluid and the second fluid.

17. A multi-fluid injection system configured to maintain an overall flow rate during a sequential delivery of at least two fluids to a patient's blood vessel, the system comprising:
   a processor configured to control the multi-fluid injection system to:
      deliver at least a first fluid into the patient's blood vessel at a first flow rate;
      deliver at least a second fluid into the patient's blood vessel at a second flow rate; and
      adjust at least one of a first flow profile of the first flow rate and a second flow profile of the second flow rate to dampen a transient increase in the overall flow rate during a transition between delivering one of the first fluid and the second fluid to delivering the other of the first fluid and the second fluid.

18. The controller of claim 17, wherein the processor is further configured to control the multi-fluid injection system to increase a transition time between delivering one of the first fluid and the second fluid and delivering the other of the first fluid and the second fluid.

19. The controller as claimed in claim 17, wherein the processor is further configured to control the multi-fluid injection system to delay the delivery of one of the first fluid and the second fluid until the other of the first fluid and the second fluid reaches a predetermined flow rate.

20. The controller as claimed in claim 17, wherein the processor is further configured to control the multi-fluid injection system to over-deliver a predetermined volume of at least one of the first fluid and the second fluid during delivery of the at least one of the first fluid and the second fluid.

* * * * *

UNITED STATES PATENT AND TRADEMARK OFFICE
CERTIFICATE OF CORRECTION

PATENT NO. : 10,898,638 B2  
APPLICATION NO. : 16/081202  
DATED : January 26, 2021  
INVENTOR(S) : Spohn et al.

Page 1 of 1

It is certified that error appears in the above-identified patent and that said Letters Patent is hereby corrected as shown below:

In the Specification
In Column 16, Line 24, delete "4-Viscosity" and insert -- Δ-Viscosity --, therefor.
In Column 16, Line 25, delete "4-Viscosity" and insert -- Δ-Viscosity --, therefor.
In Column 18, Line 61, delete "rates in" and insert -- rates --, therefor.
In Column 23, Line 31, delete "plunger 32" and insert -- plunger 36 --, therefor.
In Column 24, Line 60, delete "first fluid 32" and insert -- first fluid 30 --, therefor.

In the Claims
In Column 30, Line 9, in Claim 18, delete "controller" and insert -- system --, therefor.
In Column 30, Line 14, in Claim 19, delete "controller" and insert -- system --, therefor.
In Column 30, Line 19, in Claim 20, delete "controller" and insert -- system --, therefor.

Signed and Sealed this  
First Day of June, 2021

Drew Hirshfeld  
*Performing the Functions and Duties of the*  
*Under Secretary of Commerce for Intellectual Property and*  
*Director of the United States Patent and Trademark Office*